United States Patent
Couto et al.

(10) Patent No.: US 11,814,615 B2
(45) Date of Patent: Nov. 14, 2023

(54) METHODS AND COMPOSITIONS FOR PRESERVING BACTERIA

(71) Applicant: Vedanta Biosciences, Inc., Cambridge, MA (US)

(72) Inventors: Daniel E. Couto, Concord, MA (US); Shilpa Reddy, Watertown, MA (US); Jil Ulrich, Medford, MA (US); Scott Michonski, Belmont, MA (US)

(73) Assignee: Vedanta Biosciences, Inc., Cambridge, MA (US)

( * ) Notice: Subject to any disclaimer, the term of this patent is extended or adjusted under 35 U.S.C. 154(b) by 0 days.

(21) Appl. No.: 17/822,860

(22) Filed: Aug. 29, 2022

(65) Prior Publication Data

US 2023/0159883 A1    May 25, 2023

Related U.S. Application Data

(63) Continuation of application No. 16/341,583, filed as application No. PCT/US2017/058746 on Oct. 27, 2017, now Pat. No. 11,447,738.

(60) Provisional application No. 62/414,489, filed on Oct. 28, 2016.

(51) Int. Cl.
    *C12N 1/04*     (2006.01)
    *C12N 1/20*     (2006.01)
    *C12Q 1/06*     (2006.01)

(52) U.S. Cl.
    CPC .............. *C12N 1/04* (2013.01); *C12N 1/20* (2013.01); *C12Q 1/06* (2013.01)

(58) Field of Classification Search
    None
    See application file for complete search history.

(56) References Cited

U.S. PATENT DOCUMENTS

| | | | |
|---|---|---|---|
| 5,106,743 | A | 4/1992 | Franzblau et al. |
| 5,891,709 | A | 4/1999 | Stern et al. |
| 11,447,738 | B2 | 9/2022 | Couto et al. |
| 2010/0297231 | A1 | 11/2010 | Vehring et al. |
| 2011/0217368 | A1 | 9/2011 | Prakash et al. |
| 2014/0206067 | A1 | 7/2014 | Georgieva et al. |
| 2014/0341921 | A1 | 11/2014 | Honda et al. |
| 2015/0258188 | A1 | 9/2015 | Pizza et al. |
| 2015/0267245 | A1 | 9/2015 | Hogan et al. |
| 2018/0223244 | A1 | 8/2018 | Ananta et al. |

FOREIGN PATENT DOCUMENTS

| | | |
|---|---|---|
| CN | 102260635 A | 11/2011 |
| WO | WO 2012/098358 A1 | 7/2012 |
| WO | WO 2013/068568 A1 | 5/2013 |

OTHER PUBLICATIONS

[No Author Listed], ATCC Medium: 1016 Chopped Meat Carbohydrate Medium. Nov. 23, 2014. Retrieved from web.archive.org/web/20141123091848if. Accessed on May 18, 2020. 1 page.
[No Author] Sigma. Sigma Aldrich BioUltra Biological Buffers Webpage. Accessible at https://www.sigmaaldrich.com/life-science/metabolomics/bioultra-reagents/biological-buffers.html. Retrieved on Dec. 29, 2020. 6 pages.
Staab et al., Viability of lyophilized anaerobes in two media. Cryobiology. Apr. 1987;24(2):174-8. doi: 10.1016/0011-2240(87)90020-4.

*Primary Examiner* — David W Berke-Schlessel
(74) *Attorney, Agent, or Firm* — Wolf, Greenfield & Sacks, P.C.

(57) ABSTRACT

The disclosure provides methods and compositions for the preservation of bacteria.

20 Claims, 6 Drawing Sheets

Specification includes a Sequence Listing.

Formulation Conditions

A - Trehalose 7.5%, 20 mM Histidine, pH 7.0, 1% Yeast extract, 0.05% Cysteine, 300 mOsmo/kg B - Sucrose 7%, 20 mM Histidine, pH 7.0, 1% Yeast extract, 0.05% Cysteine, 300 mOsmo/kg

| Bacterial Strain | Initial CFU | Post Lyo CFU (Condition A) | Post Freeze Thaw (Condition A) | Post Lyo CFU (Condition B) | Post Freeze Thaw (Condition B) |
|---|---|---|---|---|---|
| 01 | $1.04 \times 10^8$ | $5 \times 10^7$ | $3 \times 10^7$ | $2 \times 10^6$ | $8 \times 10^7$ |
| 02 | $2.16 \times 10^8$ | $1 \times 10^8$ | $7 \times 10^9$ | $1.5 \times 10^8$ | $1.4 \times 10^{10}$ |
| 03 | $8.1 \times 10^8$ | $8 \times 10^7$ | $3.1 \times 10^{10}$ | $7.5 \times 10^9$ | $1 \times 10^{10}$ |
| 04 | $9.6 \times 10^8$ | $3 \times 10^8$ | $3.2 \times 10^9$ | $3.05 \times 10^9$ | $1.2 \times 10^9$ |
| 05 | $6.7 \times 10^7$ | $1.2 \times 10^9$ | $2.5 \times 10^{10}$ | $1 \times 10^9$ | $2 \times 10^{10}$ |
| 06 | $1.4 \times 10^7$ | $4.4 \times 10^5$ | N/A | $1 \times 10^6$ | $8 \times 10^5$ |
| 07 | $2.75 \times 10^9$ | $4 \times 10^9$ | $5 \times 10^9$ | $4 \times 10^{10}$ | Lawn on $10^7$ |
| 08 | $1.65 \times 10^8$ | $3.1 \times 10^8$ | $3.1 \times 10^9$ | $4.1 \times 10^8$ | $2.4 \times 10^{10}$ |

| Formulation # | Buffer / pH | Mannitol | Trehalose | Sorbitol | Sucrose | Lactose | Osmolality |
|---|---|---|---|---|---|---|---|
| 1 | His / 6.5 | 4% | | | | | 318 |
| 2 | His / 7.0 | 4% | | | | | 314 |
| 3 | Tris / 7.0 | 4% | | | | | 307 |
| 4 | Tris / 7.5 | 4% | | | | | 300 |
| 5 | His / 6.5 | | 8% | | | | 304 |
| 6 | His / 7.0 | | 8% | | | | 302 |
| 7 | Tris / 7.0 | | 8% | | | | 312 |
| 8 | Tris / 7.5 | | 8% | | | | 318 |
| 9 | His / 6.5 | | | | 8% | | 316 |
| 10 | His / 7.0 | | | | 8% | | 317 |
| 11 | Tris / 7.0 | | | | 8% | | 308 |
| 12 | His / 7.0 | | | | 8% | | 309 |
| 13 | His / 7.0 | | | 4% | | | 304 |
| 14 | Tris / 7.0 | | | 4% | | | 292 |
| 15 | His / 7.0 | 4% | | | | 4% | 329 |
| 16 | Culture media | | | | | | |

Figure 2

| Formulation # | Buffer / pH | Mannitol | Trehalose | Sorbitol | Sucrose | Lactose | Viability (CFU) |
|---|---|---|---|---|---|---|---|
| 1 | His / 6.5 | 4% | | | | | 0 |
| 2 | His / 7.0 | 4% | | | | | 0 |
| 3 | Tris / 7.0 | 4% | | | | | 0 |
| 4 | Tris / 7.5 | 4% | | | | | 0 |
| 5 | His / 6.5 | | 8% | | | | 2.8 x 10^3 |
| 6 | His / 7.0 | | 8% | | | | 9.5 x 10^4 |
| 7 | Tris / 7.0 | | 8% | | | | 1.0 x 10^4 |
| 8 | Tris / 7.5 | | 8% | | | | 1.7 x 10^5 |
| 9 | His / 6.5 | | | | 8% | | ~150 |
| 10 | His / 7.0 | | | | 8% | | 3.1 x 10^5 |
| 11 | Tris / 7.0 | | | | 8% | | 2.9 x 10^4 |
| 12 | Tris / 7.5 | | | | 8% | | 2.3 x 10^5 |
| 13 | His / 7.0 | | | 4% | | *Poor Cake* | 6.4 x 10^4 |
| 14 | Tris / 7.0 | | | 4% | | | 2.3 x 10^5 |
| 15 | His / 7.0 | 4% | | | | 4% | 0 |
| 16 | media | | | | | | ~350 |

Figure 4

Formulation Conditions

A - Trehalose 7.5%, 20 mM Histidine, pH 7.0, 1% Yeast extract, 0.05% Cysteine, 300 mOsmo/kg B - Sucrose 7%, 20 mM Histidine, pH 7.0, 1% Yeast extract, 0.05% Cysteine, 300 mOsmo/kg

| Bacterial Strain | Initial CFU | Post Lyo CFU (Condition A) | Post Freeze Thaw (Condition A) | Post Lyo CFU (Condition B) | Post Freeze Thaw (Condition B) |
|---|---|---|---|---|---|
| 01 | $1.04 \times 10^8$ | $5 \times 10^7$ | $3 \times 10^7$ | $2 \times 10^6$ | $8 \times 10^7$ |
| 02 | $2.16 \times 10^8$ | $1 \times 10^8$ | $7 \times 10^9$ | $1.5 \times 10^8$ | $1.4 \times 10^{10}$ |
| 03 | $8.1 \times 10^8$ | $8 \times 10^9$ | $3.1 \times 10^{10}$ | $7.5 \times 10^9$ | $1 \times 10^{10}$ |
| 04 | $9.6 \times 10^8$ | $3 \times 10^8$ | $3.2 \times 10^9$ | $3.05 \times 10^9$ | $1.2 \times 10^9$ |
| 05 | $6.7 \times 10^7$ | $1.2 \times 10^9$ | $2.5 \times 10^{10}$ | $1 \times 10^9$ | $2 \times 10^{10}$ |
| 06 | $1.4 \times 10^7$ | $4.4 \times 10^5$ | N/A | $1 \times 10^6$ | $8 \times 10^5$ |
| 07 | $2.75 \times 10^9$ | $4 \times 10^9$ | $5 \times 10^9$ | $4 \times 10^{10}$ | Lawn on $10^7$ |
| 08 | $1.65 \times 10^8$ | $3.1 \times 10^8$ | $3.1 \times 10^9$ | $4.1 \times 10^8$ | $2.4 \times 10^{10}$ |

Figure 5

SEQUENCE LISTING

```
Sequence total quantity: 8
SEQ ID NO: 1              moltype = DNA   length = 1530
FEATURE                   Location/Qualifiers
source                    1..1530
                          mol_type = genomic DNA
                          organism = Clostridium bolteae
SEQUENCE: 1
atgagagttt gatcctggct caggatgaac gctggcggcg tgcctaacac atgcaagtcg   60
aacgaagcaa ttaaaatgaa gttttcggat ggattttga  ttgactgagt ggcggacggg  120
tgagtaacgc gtggataacc tgcctcacac tgggggataa cagttagaaa tgactgctaa  180
taccgcataa gcgcacagta ccgcatggta cggtgtgaaa aactccggtg gtgtgagatg  240
gatccgcgtc tgattagcca gttggcgggg taacggccca ccaaagcgac gatcagtagc  300
cgacctgaga gggtgaccgg ccacattggg actgagacac ggcccaaact cctacgggag  360
gcagcagtgg ggaatattgc acaatgggcg aaagcctgat gcagcgacgc cgcgtgagtg  420
aagaagtatt tcggtatgta aagctctatc agcagggaag aaaatgacta tacctgacta  480
agaagccccg gctaactacg tgccagcagc cgcggtaata cgtaggggc  aagcgttatc  540
cggatttact gggtgtaaag ggagcgtaga cggcgaagca agtctgaagt gaaaacccag  600
ggctcaaccc tgggactgct ttggaaactg ttttgctaga gtgtcggaga ggtaagtgga  660
attcctagtg tagcggtgaa atgcgtagat attaggagga acaccagtgg cgaaggcggc  720
ttactggacg ataactgacg ttgaggctcg aaagcgtggg gagcaaacag gattagatac  780
cctggtagtc cacgccgtaa acgatgaatg ctaggtgttg gggggcaaag cccttcggtg  840
ccgtcgcaaa cgcagtaagc attccacctg gggagtacgt tcgcaagaat gaaactcaaa  900
ggaattgacg gggacccgca caagcggtgg agcatgtggt ttaattcgaa gcaacgcgaa  960
gaaccttacc aagtcttgac atcctcttga ccggctgtca acggcgcctt cccttcgggg 1020
caagagagac aggtggtgca tggttgtcgt cagctcgtgt cgtgagatgt tgggttaagt 1080
cccgcaacga gcgcaaccct tatccttagt agccagcagg taaagctggg cactctaggg 1140
agactgccag ggataacctg gaggaaggtg gggatgacgt caaatcatca tgcccttat  1200
gatttgggct acacacgtgc tacaatggcg taaacaaagg gaagcaagac agtgatgtgg 1260
agcaaatccc aaaaataacg tcccagttcg gactgtagtc tgcaacccga ctacacgaag 1320
ctggaatcgc tagtaatcgc gaatcagaat gtcgcggtga atacgttccc gggtcttgta 1380
cacaccgccc gtcacaccat gggagtcagc aacgcccgaa gtcagtgacc caactcgcaa 1440
gagagggagc tgccgaaggc ggggcaggta actggggtga agtcgtaaca aggtagccgt 1500
atcggaaggt gcggctggat cacctccttt                                   1530

SEQ ID NO: 2              moltype = DNA   length = 1522
FEATURE                   Location/Qualifiers
source                    1..1522
                          mol_type = genomic DNA
                          organism = Anaerotruncus colihominis
SEQUENCE: 2
tcaaagagtt tgatcctggc tcaggacgaa cgctggcggc gcgcctaaca catgcaagtc   60
gaacggagct tacgttttga agttttcgga tggatgaatg taagcttagt ggcggacggg  120
tgagtaacac gtgagcaacc tgcctttcag aggggggataa cagccggaaa cggctgctaa  180
taccgcatga tgttgcgggg gcacatgccc ctgcaaccaa aggagcaatc cgctgaaaga  240
tgggctcgcg tccgattagc cagttggcgg ggtaacggcc caccaaagcg acgatcggta  300
gccggactga gaggttgaac ggccacattg gactgagac  acgcccaga  ctcctacggg  360
aggcagcagt gggggatatt gcacaatggg cgaaagcctg atgcagcgac gccgcgtgag  420
ggaagacggt cttcggattg taaacctctg tctttggaga agaaaatgac ggtacccaaa  480
gaggaagctc cggctaacta cgtgccagca gccgcggtaa tacgtaggga gcaagcgttg  540
tccggaatta ctgggtgtaa agggagcgta ggcgggatgg caagtagaat gttaaatcca  600
tcggctcaac cggtggctgc gttctaaact gccgttcttg agtgaagtag aggcaggcgg  660
aattcctagt gtagcggtga aatgcgtaga tattaggagg aacaccagtg gcgaaggcgg  720
cctgctgggc tttaactgac gctgaggctc gaaagcgtgg ggagcaaaca ggattagata  780
ccctggtagt ccacgccgta aacgatgatt actaggtgtg gggggactga ccccttccgt  840
gccgcagtta acacaataag taatccacct ggggagtacg ccgcaaggt  tgaaactcaa   900
aggaattgac ggggcccgc  acaagcagtg gagtatgtgg tttaattcga agcaacgcga  960
agaaccttac caggtcttga catcggatgc atagcctaga gataggtgaa gccttcggg  1020
gcatccagac aggtggtgca tggttgtcgt cagctcgtgt cgtgagatgt tgggttaagt 1080
cccgcaacga gcgcaaccct tattattagt tgctacgcaa gagcactcta atgagactgc 1140
cgttgacaaa acggaggaag gtgggatga  cgtcaaatca tcatgcccct tatgacctgg 1200
gctacacacg tactacaatg gcactaaaac agagggcgc  acaccgcga  ggtgaagcga 1260
atcccgaaaa agtgtctcag ttcagattgc aggctgcaac ccgcctgcat gaagtcgaa  1320
ttgctagtaa tcgcggatca gcatgccgcg gtgaatacgt tcccgggcct tgtacacacc 1380
gcccgtcaca ccatggagt  cggtaacacc cgaagccagt agcctaaccg caaggggggc 1440
gctgtcgaag gtgggattga tgactggggt gaagtcgtaa caaggtagcc gtatcggaag 1500
gtgcggctgg atcacctcct tt                                          1522

SEQ ID NO: 3              moltype = DNA   length = 1529
FEATURE                   Location/Qualifiers
source                    1..1529
                          mol_type = genomic DNA
                          organism = Ruminococcus torques
SEQUENCE: 3
tacgagagtt tgatcctggc tcaggatgaa cgctggcggc gtgcctaaca catgcaagtc   60
gagcgaagcg ctgttttcag aatcttcgga ggaagaggac agtgactgag cggcggacgg  120
gtgagtaacg cgtgggcaac ctgcctcata caggggggata acagttagaa atgactgcta  180
ataccgcata agcgcacagg accgcatggt gtagtgtgaa aaactccggt ggtatgagat  240
ggacccgcgt ctgattaggt agttggtggg gtaaaggcct accaagccga cgatcagtag  300
```

```
ccgacctgag agggtgaccg gccacattgg gactgagaca cggcccaaac tcctacggga    360
ggcagcagtg gggaatattg cacaatgggg gaaaccctga tgcagcgacg ccgcgtgaag    420
gaagaagtat tcggtatgt aaacttctat cagcagggaa gaaaatgacg gtacctgagt    480
aagaagcacc ggctaaatac gtgccagcag ccgcggtaat acgtatggtg caagcgttat    540
ccggatttac tgggtgtaaa gggagcgtag acggatagcg aagtctgatg tgaaaaccca    600
gggctcaacc ctgggactgc tttgaaact gcagatctgg agtgccggag aggtaagcgg    660
aattcctagt gtagcggtga atgcgtaga tattaggagg aacaccagtg gcgaaggcgg    720
cttactggac ggtgactgac gttgaggctc gaaagcgtgg ggagcaaaca ggattagata    780
ccctggtagt ccacgccgta aacgatgact actaggtgtc ggtgtgcaaa gcacatcggt    840
gccgcagcaa acgcaataag tagtccacct ggggagtacg ttcgcaagaa tgaaactcaa    900
aggaattgac ggggacccgc acaagcggtg gagcatgtgg tttaattcga agcaacgcga    960
agaaccttac ctggtcttga catccggatg acgggcgagt aatgtcgccg tcccttcggg   1020
gcgtccgaga caggtggtgc atggttgtcg tcagctcgtg tcgtgagatg tgggttaag   1080
tcccgcaacg agcgcaaccc ttatcttcag tagccagcat ataaggtggg cactctgaca   1140
agactgccag ggagaacctg gaggaaggtg gggatgacgt caaatcatca tgccccttat   1200
ggccagggct acacacgtgc tacaatggcg taaacaaagg gaagcgagag ggtgacctga   1260
agcgaatccc aaaaataacg tctcagttcg gattgtagtc tgcaactcga ctacatgaag   1320
ctggaatcgc tagtaatcgc ggatcagcat gccgcggtga atacgttccc ggtcttgta   1380
cacaccgccc gtcacaccat gggagtcagt aacgcccgaa gccagtgacc caaccttaga   1440
ggagggagct gtcgaaggcg ggacggataa ctggggtgaa gtcgtaacaa ggtagccgta    1500
tcggaaggtg cggctggatc acctcctttt                                    1529

SEQ ID NO: 4             moltype = DNA   length = 1527
FEATURE                  Location/Qualifiers
source                   1..1527
                         mol_type = genomic DNA
                         organism = Clostridium symbiosum
SEQUENCE: 4
atgagagttt gatcctggct caggatgaac gctggcggcg tgcctaacac atgcaagtcg     60
aacgaagcga tttaacggaa gttttcggat ggaagttgaa ttgactgagt ggcggacggg    120
tgagtaacgc gtgggtaacc tgccttgtac tggggacaa cagttagaaa tgactgctaa    180
taccgcataa gcgcacagta tcgcatgata cagtgtgaaa aactccggtg gtacaagatg    240
gacccgcgtc tgattagcta gttggtaagg taacggctta ccaaggcgac gatcagtagc    300
cgacctgaga gggtgaccgg ccacattggg actgagacac ggcccaaact cctacggagg    360
gcagcagtgg ggaatattgc acaatgggcg aaagcctgat gcagcgacgc cgcgtgagtg    420
aagaagtatt tcggtatgta agctctatc agcaggaag aaaatgacgg tacctgacta    480
agaagccccg gctaactacg tgccagcagc cgcggtaata cgtagggggc aagcgttatc    540
cggatttact gggtgtaaag ggagcgtaga cggtaaagca agtctgaagt gaaagcccgc    600
ggctcaactg cgggactgct ttgaaactgt gtcggaga gtaagtgga    660
attcctagtg tagcggtgaa atgcgtagat attaggagga acaccagtgg cgaaggcgac    720
ttactggacg ataactgacg ttgaggctcg aaagcgtggg gagcaaacag gattagatac    780
cctggtagtc cacgccgtaa acgatgaata ctaggtgttg gggagcaaag ctcttcggtg    840
ccgtcacaaa cgcagtaagt attccacctg gggagtacgt tcgcaagaat gaaactcaaa    900
ggaattgacg ggacccgca caagcggtgg agcatgtggt ttaattcgaa gcaacgcgaa    960
gaaccttacc aggtcttgac atcgatccga cgggggagta cgtcccctt cccttcgggg   1020
cggagaagac aggtggtgca tggttgtcgt cagctcgtgt cgtgagatgt gggttaagt   1080
cccgcaacga gcgcaaccct tattctaagt agccagcggt tcggccggga actcttggga   1140
gactgccagg gataacctgg aggaaggtgg ggatgacgtc aaatcatcat gccccttatg   1200
atctgggcta cacacgtgct acaatggcgt aaacaaagag aagcaagacc gcgaggtgga   1260
gcaaatctca aaaataacgt ctcagttcgg actgcaggct gcaactcgcc tgcacgaagc   1320
tggaatcgct agtaatcgcg aatcagaatg tcgcggtgaa tacgttcccg ggtcttgtac   1380
acaccgcccg tcacaccatg ggagtcagta acgcccgaag tcagtgaccc aaccgcaagg   1440
agggagctgc cgaaggcggg accgataact gggggtgaagt cgtaacaagg tagccgtatc   1500
ggaaggtgcg gctggatcac ctccttt                                      1527

SEQ ID NO: 5             moltype = DNA   length = 1531
FEATURE                  Location/Qualifiers
source                   1..1531
                         mol_type = genomic DNA
                         organism = Blautia producta
SEQUENCE: 5
atcagagagt ttgatcctgg ctcaggatga acgctggcgg cgtgcttaac acatgcaagt     60
cgagcgaagc acttaagtgg atctcttcgg attgaagctt atttgactga gcggcggacg    120
ggtgagtaac gcgtgggtaa cctgcctcat acagggggat aacagttaga aatgctgcta    180
aataccgcat aagcgcacag gaccgcatgg tctggtgtga aaaactccgg tggtatgaga    240
tggacccgcg tctgattagc tagttggagg ggtaacggcc caccaaggcg acgatcagta    300
gccggcctga gagggtgaac ggccacattg gactgagaca cggcccagac tcctacgggg    360
aggcagcagt ggggaatatt gcacaatggg ggaaaccctg atgcagcgac gccgcgtgaa    420
ggaagaagta tctcggtatg taaacttcta tcagcaggaa agaaaatgac ggtacctgac    480
taagaagccc cggctaacta cgtgccagca gccgcggtaa tacgtagggg gcaagcgtta    540
tccggattta ctgggtgtaa agggagcgta gacggaagag caagtctgat gtgaaaggct    600
ggggcttaac cccaggactg cattggaaac tgttttcta gagtgccgga gaggtaagcg    660
gaattcctag tgtagcggtg aaatgcgtag atattaggaa gaacaccagt ggcgaaggcg    720
gcttactgga caataactga cgttgaggct cgaaagcaaa aggattagat    780
accctggtag tccacgccgt aaacgatgaa tactaggtgt cgggtggcaa agccattcgg    840
tgccgcagca aacgcaataa gtattccacc tggggagtac gttcgcaaga tgaaactcaa    900
aggaattgac gggggacccg cacaagcggt ggagcatgtg gtttaattcg aagcaacgcg    960
aagaaccttac caagtcttg acatccctct gaccggcccg taacgggcc ttcccttcgg   1020
ggcagaggag acaggtggtg catggttgtc gtcagctcgt gtcgtgagat gttgggttaa   1080
```

```
gtcccgcaac gagcgcaacc cctatcctta gtagccagca ggtgaagctg ggcactctag   1140
ggagactgcc ggggataacc cggaggaagg cggggacgac gtcaaatcat catgcccctt   1200
atgatttggg ctacacacgt gctacaatgg cgtaaacaaa gggaagcgag acagcgatgt   1260
tgagcaaatc ccaaaaataa cgtcccagtt cggactgcag tctgcaactc gactgcacga   1320
agctggaatc gctagtaatc gcgaatcaga atgtcgcggt gaatacgttc ccgggtcttg   1380
tacacaccgc ccgtcacacc atgggagtca gtaacgcccg aagtcagtga cccaacctta   1440
caggagggag ctgccgaagg cgggaccgat aactggggtg aagtcgtaac aaggtagccg   1500
tatcggaagg tgcggctgga tcacctcctt t                                 1531

SEQ ID NO: 6              moltype = DNA  length = 1529
FEATURE                   Location/Qualifiers
source                    1..1529
                          mol_type = genomic DNA
                          organism = Dorea longicatena
SEQUENCE: 6
aacgagagtt tgatcctggc tcaggatgaa cgctggcggc gtgcttaaca catgcaagtc   60
gagcgaagca cttaagtttg attcttcgga tgaagacttt tgtgactgag cggcggacgg   120
gtgagtaacg cgtgggtaac ctgcctcata caggggata acagttagaa atgactgcta   180
ataccgcata agaccacggt accgcatggt acagtggtaa aaactccggt ggtatgagat   240
ggacccgcgt ctgattaggt agttggtggg gtaacggcct accaagccga cgatcagtag   300
ccgacctgag agggtgaccg gccacattgg gactgagaca cggcccagac tcctacggga   360
ggcagcagtg gggaatattg cacaatggag gaaactctga tgcagcgacg ccgcgtgaag   420
gatgaagtat ttcggtatgt aaacttctat cagcagggaa gaaaatgacg gtacctgact   480
aagaagcccc ggctaactac gtgccagcag ccgcggtaat acgtaggggg caagcgttat   540
ccggatttac tgggtgtaaa gggagcgtag acggcacggc aagccagatg tgaaagcccg   600
gggctcaacc ccgggactgc atttggaact gctgagctag agtgtcggag aggcaagtgg   660
aattcctagt gtagcggtga aatgcgtaga tattaggagg aacaccagtg gcgaaggcgg   720
cttgctggac gatgactgac gttgaggctc gaaagcgtgg ggagcaaaca ggattagata   780
ccctggtagt ccacgccgta aacgatgact gctaggtgtc gggtggcaaa gccattcggt   840
gccgcagcta acgcaataag cagtccacct ggggagtacg ttcgcaagaa tgaaactcaa   900
aggaattgac ggggacccgc acaagcggtg gagcatgtgg tttaattcga agcaacgcga   960
agaaccttac ctgatcttga catcccgatg accgcttcgt aatggaagct tttcttcgga   1020
acatcggtga caggtggtgc atggttgtcg tcagctcgtg tcgtgagatg ttgggttaag   1080
tcccgcaacg agcgcaaccc ctatcttcag tagccagcag gttaagctgg gcactctgaa   1140
gagactgcca gggataacct ggaggaaggt gggatgacg tcaaatcatc atgcccctta   1200
tgaccagggc tacacacgtg ctacaatggc gtaaacaaag agaagcgaac tcgcgagggt   1260
aagcaaatct caaaaataac gtctcagttc ggattgtagt ctgcaactcg actacatgaa   1320
gctggaatcg ctagtaatcg cagatcagaa tgctgcggtg aatacgttcc cgggtcttgt   1380
acacaccgcc cgtcacacca tgggagtcag taacgcccga agtcagtgac ccaaccgtaa   1440
ggagggagct gccgaaggtg ggaccgataa ctggggtgaa gtcgtaacaa ggtagccgta   1500
tcggaaggtg cggctggatc acctcctttt                                   1529

SEQ ID NO: 7              moltype = DNA  length = 1537
FEATURE                   Location/Qualifiers
source                    1..1537
                          mol_type = other DNA
                          note = Erysipelotrichaceae bacterium 21_3
                          organism = unidentified
SEQUENCE: 7
atggagagtt tgatcctggc tcaggatgaa cgctggcggc atgcctaata catgcaagtc   60
gaacgagtt tcgaggaagc ttgcttccaa agagacttag tggcgaacgg gtgagtaaca   120
cgtaggtaac ctgcccatgt gtccgggata actgctggaa acggtagcta aaaccggata   180
ggtatacaga gcgcatgctc agtatattaa agcgcccatc aaggcgtgaa catggatgga   240
cctgcgcgc attagctagt tggtgaggta acggcccacc aaggcgatga tgcgtagccg   300
gcctgagagg gtaaacggcc acattggac tgagacaccc caaactcc tacgggaggc   360
agcagtaggg aattttcgtc aatggggaa accctgaacg agcaatgccg cgtgagtgaa   420
gaaggtcttc ggatcgtaaa gctctgttgt aagtgaagaa cggctcatag gaaaatgct   480
atgggagtga cggtagctta ccagaaagcc acggctaact acgtgccagc agccgcggta   540
atacgtaggt ggcaagcgtt atccgga atc attgggcgta aaggtgcgt aggtggcgta   600
ctaagtctgt agtaaaaggc aatggctcaa ccattgtaag ctatgaaac tggtatgctg   660
gagtgcagaa gagggcgatg gaattccatg tgtagcggta aaatgcgtag atatatggag   720
gaacaccagt ggcgaaggcg gtcgcctggt ctgtaactga cactgaggca cgaaagcgtg   780
gggagcaaat aggattagat accctagtag tccacgccgt aaacgatgag aactaagtgt   840
tggaggaatt cagtgctgca gttaacgcaa taagttctcc gcctggggag tatgcacgca   900
agtgtgaaac tcaaaggaat tgacgggggc ccgcacaagc ggtggagtat gtggtttaat   960
tcgaagcaac gcgaagaacc ttaccaggcc ttgacatgga aacaaatacc ctagagatag   1020
ggggataatt atggatcaca caggtggtgc atggttgtcg tcagctcgtg tcgtgagatg   1080
ttgggttaag tcccgcaacg agcgcaaccc ttgtcgcatg ttaccagcat caagttgggg   1140
actcatgcga gactgccggt gacaaaccgg aggaaggtgg ggatgacgtc aaatcatcat   1200
gccccttatg gcctgggcta cacacgtact acaatggcgg ccacaaagag cagcgacaca   1260
gtgatgtgaa gcgaatctca taaggtcgt ctcagttcgg attgaagtct gcaactcgac   1320
ttcatgaagt cggaatcgct agtaatcgca gatcagcatg ctgcggtgaa tacgttctcg   1380
ggccttgtac acaccgcccg tcaaccatgg gagtcagtaa tacccgaagc cggtggcat   1440
aaccgtaagg agtgagccgt cgaaggtagg accgatgact gggggttaagt cgtaacaagg   1500
tatccctacg ggaacgtggg gatggatcac ctccttt                           1537

SEQ ID NO: 8              moltype = DNA  length = 1530
FEATURE                   Location/Qualifiers
source                    1..1530
```

```
                    mol_type = other DNA
                    note = Subdoligranulum spp
                    organism = unidentified
SEQUENCE: 8
tattgagagt ttgatcctgg ctcaggatga acgctggcgg cgtgcttaac acatgcaagt    60
cgaacggggt gctcatgacg gaggattcgt ccaacggatt gagttaccta gtggcggacg   120
ggtgagtaac gcgtgaggaa cctgccttgg agaggggaat aacactccga aaggagtgct   180
aataccgcat gatgcagttg ggtcgcatgg ctctgactgc caaagattta tcgctctgag   240
atggcctcgc gtctgattag ctagtaggcg gggtaacggc ccacctaggc gacgatcagt   300
agccggactg agaggttgac cggccacatt gggactgaga cacggcccag actcctacgg   360
gaggcagcag tggggaatat tgggcaatgg gcgcaagcct gacccagcaa cgccgcgtga   420
aggaagaagg ctttcgggtt gtaaacttct tttgtcgggg acgaaacaaa tgacggtacc   480
cgacgaataa gccacggcta actacgtgcc agcagccgcg gtaatacgta ggtggcaagc   540
gttatccgga tttactgggt gtaaagggcg tgtaggcggg attgcaagtc agatgtgaaa   600
actgggggct caacctccag cctgcatttg aaactgtagt tcttgagtgc tggagaggca   660
atcggaattc cgtgtgtagc ggtgaaatgc gtagatatac ggaggaacac cagtggcgaa   720
ggcggattgc tggacagtaa ctgacgctga ggcgcgaaag cgtggggagc aaacaggatt   780
agataccctg gtagtccacg ccgtaaacga tggatactag gtgtgggggg tctgaccccc   840
tccgtgccgc agttaacaca ataagtatcc cacctgggga gtacgatcgc aaggttgaaa   900
ctcaaaggaa ttgacggggg cccgcacaag cggtggagta tgtggtttaa ttcgaagcaa   960
cgcgaagaac cttaccaggg cttgacatcc cactaacgaa gcagagatgc attaggtgcc  1020
cttcggggaa agtggagaca ggtggtgcat ggttgtcgtc agctcgtgtc gtgagatgtt  1080
gggttaagtc ccgcaacgag cgcaaccctt attgttagtt gctacgcaag agcactctag  1140
cgagactgcc gttgacaaaa cggaggaagg tggggacgac gtcaaatcat catgcccctt  1200
atgtcctggg ccacacacgt actacaatgg tggttaacag agggaggcaa taccgcgagg  1260
tggagcaaat ccctaaaagc catcccagtt cggattgcag gctgaaaccc gcctgtatga  1320
agttggaatc gctagtaatc gcggatcagc atgccgcggt gaatacgttc ccgggccttg  1380
tacacaccgc ccgtcacacc atgagagtcg ggaacacccg aagtccgtag cctaaccgca  1440
aggagggcgc ggccgaaggt gggttcgata attggggtga agtcgtaaca aggtagccgt  1500
atcggaaggt gcggctggat cacctccttt                                   1530
```

METHODS AND COMPOSITIONS FOR PRESERVING BACTERIA

RELATED APPLICATIONS

This application is a continuation of U.S. application Ser. No. 16/341,583, filed Apr. 12, 2019, which is a national stage filing under 35 U.S.C. 371 of International Patent Application Serial No. PCT/US2017/058746, filed Oct. 27, 2017, which claims the benefit under 35 U.S.C. § 119(e) of U.S. provisional application No. 62/414,489, filed Oct. 28, 2016, the entire contents of each of which are incorporated by reference herein in their entirety.

REFERENCE TO AN ELECTRONIC SEQUENCE LISTING

The contents of the electronic sequence listing (P074570009US02-SEQ-NTJ.xml; Size: 20,573 bytes; and Date of Creation: Aug. 12, 2022) is herein incorporated by reference in its entirety.

FIELD OF THE INVENTION

The disclosure provides methods and compositions for the preservation of bacteria.

BACKGROUND

The human intestinal microbiome includes a large number of microorganisms. A significant number of these microorganisms are anaerobic bacteria. Compositions that include anaerobic bacteria that originated from the human intestinal microbiome have shown potential in the treatment of human disease (See e.g., Atarashi et al., *Nature* 500, 232, 2013; Atarashi et al., *Cell* 163, 1, 2015; Mathewson et al., *Nature Immunology* 17, 505, 2016). Anaerobic bacteria are challenging to preserve because of their sensitivity to oxygen.

Improved compositions and methods for the preservation of anaerobic bacteria are needed therefore.

SUMMARY

Provided herein are compositions and methods for the preservation of bacteria. Bacteria can be preserved through lyophilization (freeze-drying), which allows for the long-term storage of bacteria, including therapeutic amounts of bacteria. In one aspect, the disclosure provides methods for the lyophilization of bacterial compositions. In one aspect, the disclosure provides compositions that allow for the lyophilization of anaerobic bacterial strains. Prior to the current disclosure, compositions comprising such bacterial strains would lose all, or most, of their viability upon lyophilization, severely impeding the options for preserving such bacterial strains in amounts sufficient for therapeutic applications. The compositions and methods provided herein allow for the first time the preservation of bacterial strains through lyophilization. The compositions disclosed herein are thought to have these desired preservative properties because of the combination of specific lyoprotectant(s), nutrient(s), and/or excipient(s). In addition or alternatively, the lyophilization cycle, such as the temperature ramp rate, may also contribute to the beneficial preservation properties of the compositions and methods described herein.

Provided herein are compositions and methods for preservation of bacteria. In one aspect, the disclosure provides a composition comprising a lyoprotectant, a nutrient, an antioxidant, and a buffer. In some embodiments of the compositions provided herein, the lyoprotectant is a sugar. In some embodiments of the compositions provided herein, the sugar is a disaccharide. In some embodiments of the compositions provided herein, the disaccharide is sucrose. In some embodiments of the compositions provided herein, the sucrose is at a concentration of sucrose is between 6.0% and 10.0%. In some embodiments of the compositions provided herein, the sucrose is at a concentration between 7.0% and 8.0%.

In some embodiments of the compositions provided herein, the disaccharide is trehalose. In some embodiments of the compositions provided herein, the trehalose is at a concentration between 6.0% and 10.0%. In some embodiments of the compositions provided herein, the trehalose is at a concentration between 7.0% and 8.0%.

In some embodiments of the compositions provided herein, the nutrient is yeast extract, Luria-Bertani broth, or plant peptone. In some embodiments of the compositions provided herein, the nutrient is yeast extract. In some embodiments of the compositions provided herein, the concentration of the yeast extract is between 0.5% and 2.0%.

In some embodiments of the compositions provided herein, the antioxidant is inulin, riboflavin, or cysteine. In some embodiments of the compositions provided herein, the antioxidant is cysteine. In some embodiments of the compositions provided herein, the concentration of cysteine is between 0.01% and 0.5%.

In some embodiments of the compositions provided herein, the buffer is a histidine buffer or a tris buffer. In some embodiments of the compositions provided herein, the buffer is a histidine buffer. In some embodiments of the compositions provided herein, the buffer is about pH 7.0. In some embodiments of the compositions provided herein, the buffer is at a concentration between 10 mM and 50 mM.

In some embodiments of the compositions provided herein, the composition has been reduced.

In some embodiments of the compositions provided herein, the composition includes trehalose, yeast extract, cysteine, and a histidine buffer. In some embodiments of the compositions provided herein, the composition includes 7.5% trehalose, 1% yeast extract, 0.05% cysteine and 20 mM histidine buffer.

In some embodiments of the compositions provided herein, the composition includes sucrose, yeast extract, cysteine and a histidine buffer. In some embodiments of the compositions provided herein, the composition includes 7.0% sucrose, 1% yeast extract, 0.05% cysteine and 20 mM histidine buffer.

Any of the compositions described herein may further comprise an excipient. In some embodiments, the excipient is a stabilizing agent. In some embodiments, the stabilizing agent is a reducing agent. In some embodiments, the reducing agent is sodium metabisulfite. In some embodiments, the sodium metabisulfite is 0.05%.

In some embodiments of the compositions provided herein, the composition includes trehalose, yeast extract, cysteine, a histidine buffer, and an excipient. In some embodiments of the compositions provided herein, the composition includes 7.5% trehalose, 1% yeast extract, 0.05% cysteine, 20 mM histidine buffer, 0.05% sodium metabisulfite. In some embodiments of the compositions provided herein, the composition includes sucrose, yeast extract, cysteine, a histidine buffer, and an excipient. In some embodiments of the compositions provided herein, the composition includes 7.0% sucrose, 1% yeast extract, 0.05% cysteine, 20 mM histidine buffer, and 0.05% sodium metabisulfite.

In some embodiments of the compositions provided herein, the composition includes bacteria of one or more families, classes, genera and/or species. In some embodiments of the compositions provided herein, the bacteria are anaerobic bacteria. In some embodiments of the compositions provided herein, the anaerobic bacteria are strict anaerobic bacteria. In some embodiments of the compositions provided herein, the anaerobic bacteria are facultative anaerobic bacteria.

In some embodiments of the compositions provided herein, the bacteria comprise one or more bacterial strains belonging to the class Clostridia. In some embodiments of the compositions provided herein, the bacteria comprise one or more bacterial strains belonging to the family Clostridiaceae. In some embodiments of the compositions provided herein, the bacteria comprise one or more bacterial strains belonging to the genus *Clostridium*. In some embodiments of the compositions provided herein, the bacteria comprise one or more bacterial strains selected from the group consisting of *Clostridium bolteae, Anaerotruncus colihominis, Ruminococcus torques, Clostridium symbiosum, Blautia producta, Dorea longicatena, Erysipelotrichaceae bacterium*, and *Subdolinogranulum* spp. In some embodiments, the one or more bacterial strains comprise one or more 16s rRNA sequences having at least 97% sequence identity with the nucleic acid sequences selected from the group consisting of SEQ ID NOs: 1-8. In some embodiments of the compositions provided herein, the composition includes at least $1 \times 10^8$ colony forming units of bacteria per milliliter of the composition.

In some embodiments of the compositions provided herein, the composition is a stabilizing composition. In some embodiments of the compositions provided herein, a stabilizing composition allows for the recovery of at least 1%, at least 10%, at least 20%, at least 30%, at least 40%, at least 50%, at least 60%, at least 70%, at least 80%, at least 90%, or up to 100% of the colony forming units of the bacteria over a period of time. In some embodiments, the period of time is at least 1 week, at least 2 weeks, at least 4 weeks, at least 2 months, at least 3 months, at least 6 months, or at least 1 year or more.

In some embodiments of the compositions provided herein, a stabilizing composition allows for the recovery of at least 1%, at least 10%, at least 20%, at least 30%, at least 40%, at least 50%, at least 60%, at least 70%, at least 80%, at least 90%, or up to 100% of the colony forming units after a specific event. In some embodiments, the specific event is one or more freeze-thaw cycle or lyophilization cycle.

In one aspect, the disclosure provides methods for preserving bacteria. In some embodiments of the methods provided herein, the method includes adding bacteria to a composition of any of the preceding claims and subjecting the composition including the bacteria to a lyophilization cycle. In some embodiments, the lyophilization cycle comprises one or more steps of a temperature ramp rate between 0.5° C./min to 3° C./min. In some embodiments, the lyophilization cycle comprises one or more steps of a temperature ramp rate is 2.5° C./min. In some embodiments, the composition further comprises assessing the bacteria in a sensitivity assay prior to adding the bacteria to the composition. In some embodiments, the sensitivity assay is a Gram stain or freeze-thaw assay. In some embodiments, if the bacteria are assessed to be sensitive, (i) an excipient is added to the composition; and/or (ii) the lyophilization cycle comprises one or more steps of a temperature ramp rate of 2.5° C./min. In some embodiments, the excipient is a stabilizing agent. In some embodiments, the stabilizing agent is a reducing agent. In some embodiments, the reducing agent is sodium metabisulfite. In some embodiments, the sodium metabisulfite is 0.05%.

In some embodiments of the methods provided herein, the method further includes measuring the number of colony forming units after subjecting the composition comprising the bacteria to the lyophilization cycle. In some embodiments of the methods provided herein, the method further includes measuring the number of colony forming units prior to subjecting the composition comprising the bacteria to the lyophilization cycle. In some embodiments of the method provided herein, the method further comprises comparing the number of colony forming units prior to subjecting the composition comprising the bacteria to the lyophilization cycle and the number of colony forming units after subjecting the composition comprising the bacteria to the lyophilization cycle, and determining a level of preservation. In some embodiments of the methods provided herein, the method results in the preservation of at least 1%, at least 10%, at least 20%, at least 30%, at least 40%, at least 50%, at least 60%, at least 70%, at least 80%, at least 90%, up to 100% of the colony forming units.

In one aspect, the disclosure provides methods for generating the compositions provided herein. In some embodiments of the methods provided herein, the method includes creating a mixture by combining the lyoprotectant, the nutrient, the antioxidant, and the buffer, reducing the mixture thereby generating the composition. In some embodiments of the methods provided herein, further comprising adding an excipient to the mixture. In some embodiments of the methods provided herein, the excipient is a stabilizing agent. In some embodiments of the methods provided herein, the stabilizing agent is a reducing agent. In some embodiments of the methods provided herein, the reducing agent is sodium metabisulfite. In some embodiments of the methods provided herein, the method further comprises adding bacteria to the mixture.

In some embodiments of the methods provided herein, the bacteria are strict anaerobic bacteria. In some embodiments of the methods provided herein, the bacteria comprise one or more bacterial strains belonging to the class Clostridia. In some embodiments of the methods provided herein, the bacteria comprise one or more bacterial strains belonging to the family Clostridiaceae. In some embodiments of the methods provided herein, the bacteria comprise one or more bacterial strains belonging to the genus *Clostridium*.

In some embodiments of the methods provided herein, the bacteria comprise one or more bacterial strains selected from the group consisting of *Clostridium bolteae, Anaerotruncus colihominis, Ruminococcus torques, Clostridium symbiosum, Blautia producta, Dorea longicatena, Erysipelotrichaceae bacterium*, and *Subdolinogranulum* spp. In some embodiments of the methods provided herein, the bacteria comprise one or more bacterial strains comprise 16S rDNA sequences having at least 97% sequence identity with the nucleic acid sequences selected from the group consisting of SEQ ID NOs: 1-8.

In some embodiments of the methods provided herein, the method further comprises assessing the bacteria in a sensitivity assay prior to adding the bacteria to the mixture. In some embodiments of the methods provided herein, the sensitivity assay is a Gram stain or a freeze-thaw assay. In some embodiments of the methods provided herein, if the bacteria are assessed to be sensitive, an excipient is added to the mixture.

In one aspect, the disclosure provides compositions comprising 7.5% trehalose, 1% yeast extract, 0.05% cysteine, 20 mM histidine buffer, and 0.05% sodium metabisulfite. In one aspect, the disclosure provides compositions comprising 7.0% sucrose, 1% yeast extract, 0.05% cysteine, 20 mM histidine buffer, and 0.05% sodium metabisulfite.

In one aspect, the disclosure provides compositions comprising 7.5% trehalose, 1% yeast extract, 0.05% cysteine, 20 mM histidine buffer, and one or more bacterial strain belonging to the class Clostridia. In one aspect, the disclosure provides compositions comprising 7.0% sucrose, 1% yeast extract, 0.05% cysteine, 20 mM histidine buffer, and one or more bacterial strain belonging to the class Clostridia. In one aspect, the disclosure provides compositions comprising 7.5% trehalose, 1% yeast extract, 0.05% cysteine, 20 mM histidine buffer, 0.05% sodium metabisulfite, and one or more bacterial strain belonging to the class Clostridia. In one aspect, the disclosure provides compositions comprising 7.0% sucrose, 1% yeast extract, 0.05% cysteine, 20 mM histidine buffer, 0.05% sodium metabisulfite, and one or more bacterial strain belonging to the class Clostridia.

These and other aspects of the invention, as well as various embodiments thereof, will become more apparent in reference to the drawings and detailed description of the invention.

Each of the limitations of the invention can encompass various embodiments of the invention. It is, therefore, anticipated that each of the limitations of the invention involving any one element or combinations of elements can be included in each aspect of the invention. This invention is not limited in its application to the details of construction and the arrangement of components set forth in the following description or illustrated in the drawings. The invention is capable of other embodiments and of being practiced or of being carried out in various ways.

BRIEF DESCRIPTION OF THE DRAWINGS

The accompanying drawings are not intended to be drawn to scale. The figures are illustrative only and are not required for enablement of the disclosure. For purposes of clarity, not every component may be labeled in every drawing. In the drawings:

FIG. 2 shows a table including formulations described in Example 1.

FIG. 4 shows a table including example formulations used in Example 1.

FIG. 5 shows a table including results described in Example 3.

DETAILED DESCRIPTION

Figure 1:
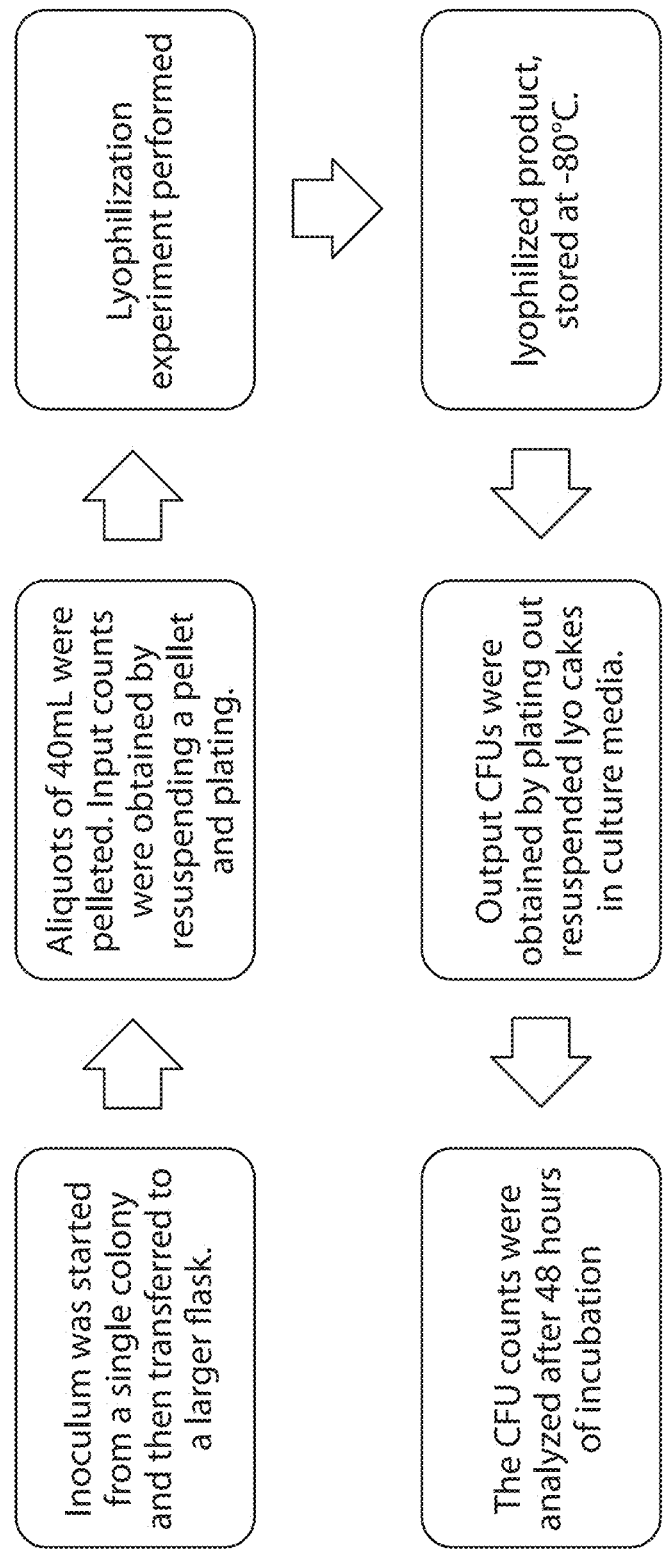
FIG. 1 shows a schematic overview of example experiments described in the Examples.

The preservation of bacterial compositions, including anaerobic bacteria, has been challenging. While bacteria can be frozen down and regrown on plates or in solution, it has been difficult to standardize this process. There is a need to preserve bacteria that can be used for therapeutic purposes. Preservation processes, such as cryopreservation and lyophilization, have been well established for aerobic bacteria, and many factors that affect survival and recovery of aerobic bacteria in the preservation process are understood (Prakash et al. *FEMS Microbiol Lett* (2013) 339:1-9). However, the development of preservation processes for use with anaerobic bacteria are not sufficient. Such development and research using anaerobic bacteria is hindered by the significant difficulties of working with anaerobic bacteria (Mori et al. "The Challenges of Studying the Anaerobic Microbial World" *Microbes Environ.* (2014) 29(4) 335-337). Given that anaerobic bacteria, such as bacterial strains obtained from the human intestinal microbiome have shown potential in the treatment of human disease, improved methods for preserving anaerobic bacteria that allow for high levels of bacterial recovery are needed.

Lyophilization is a recognized process for the preservation of peptides and proteins, and may be used in the preparation of therapeutic compositions to be resuspended and administered to subjects. However, lyophilization of bacterial compositions, in particular anaerobic bacteria, has been challenging. This disclosure, for the first time provides compositions that allow for the lyophilization of anaerobic bacteria without a loss of viability. The disclosure also provides compositions and methods for preserving bacteria that are considered to be sensitive and difficult to preserve without substantial loss of viability. The disclosure teaches that formulations that include certain lyoprotectants, such as disaccharides e.g., trehalose and sucrose, allow for the preservation of anaerobic bacteria, while closely related lyoprotectants, such as mannitol and sorbitol, do not.

Further, many proposed methods for generating lyophilized compositions containing bacteria include animal-derived products. For example, Staab et al. report freeze-drying (lyophilizing) anaerobic bacteria using chopped meat carbohydrate broth supplemented with 12% sucrose or double strength skim milk (Staab et al. *Cryobiology* (1987) 24:174-178). Phillips et al. demonstrated that many of the anaerobic rumen bacteria tested retained viability after drying in horse serum supplemented with glucose (Philips, et al. *J. Appl. Bact.* (1975) 38:319-322). Finally, Šourek recommends a mixture of calf serum or defibrinated sheep blood and lactose for lyophilization of most bacteria (Šourek, *Int. J. Sys. Bacteriol.* (1974) 24(3):358-365). Important for administration of therapeutic products to human subjects, the compositions described herein do not include animal products or animal-derived products.

This invention is not limited in its application to the details of construction and the arrangement of components set forth in the following description or illustrated in the drawings. The invention is capable of other embodiments and of being practiced or of being carried out in various ways. Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

Provided herein are compositions and methods for the preservation of bacteria. In one aspect, the disclosure provides a composition comprising a lyoprotectant, a nutrient, an antioxidant, and a buffer. In some embodiments, the compositions also comprise an excipient, such as a stabilizing agent. In some embodiments of the compositions provided herein, the lyoprotectant is a sugar. In some embodiments of the compositions provided herein, the sugar is a disaccharide, such as sucrose, trehalose, lactose, maltose, cellobiose, chitobiose, or lactulose. In some embodiments, the composition does not include mannitol. In some embodiments, the composition does not include sorbitol.

In some embodiments of the compositions provided herein, the disaccharide is sucrose. In some embodiments of the compositions provided herein, the sucrose is at a concentration between 6.0% and 10.0%, inclusive, such as 6.0%, 6.1%, 6.2%, 6.3%, 6.4%, 6.5%, 6.6%, 6.7%, 6.8%, 6.9%, 7.0%, 7.1%, 7.2%, 7.3%, 7.4%, 7.5%, 7.6%, 7.7%, 7.8%, 7.9%, 8.0%, 8.1%, 8.2%, 8.3%, 8.4%, 8.5%, 8.6%, 8.7%, 8.8%, 8.9%, 9.0%, 9.1%, 9.2%, 9.3%, 9.4%, 9.5%, 9.6%, 9.7%, 9.8%, 9.9%, 9.0%, or 10.0%. In some embodiments of the compositions provided herein, the sucrose is at a concentration between 7.0% and 8.0%, inclusive, such as 7.0%, 7.1%, 7.2%, 7.3%, 7.4%, 7.5%, 7.6%, 7.7%, 7.8%, 7.9%, or 8.0%.

In some embodiments of the compositions provided herein, the disaccharide is trehalose. In some embodiments of the compositions provided herein, the trehalose is at a concentration between 6.0% and 10.0%, inclusive, such as 6.0%, 6.1%, 6.2%, 6.3%, 6.4%, 6.5%, 6.6%, 6.7%, 6.8%, 6.9%, 7.0%, 7.1%, 7.2%, 7.3%, 7.4%, 7.5%, 7.6%, 7.7%, 7.8%, 7.9%, 8.0%, 8.1%, 8.2%, 8.3%, 8.4%, 8.5%, 8.6%, 8.7%, 8.8%, 8.9%, 9.0%, 9.1%, 9.2%, 9.3%, 9.4%, 9.5%, 9.6%, 9.7%, 9.8%, 9.9%, 9.0%, or 10.0%. In some embodiments of the compositions provided herein, the trehalose is at a concentration between 7.0% and 8.0%, inclusive, such as 7.0%, 7.1%, 7.2%, 7.3%, 7.4%, 7.5%, 7.6%, 7.7%, 7.8%, 7.9%, or 8.0%. In some embodiments of the compositions provided herein, the nutrient is yeast extract, Luria-Bertani broth, or plant peptone. In some embodiments of the compositions provided herein, the nutrient is yeast extract. In some embodiments of the compositions provided herein, the concentration of the yeast extract is between 0.5% and 2.0%, inclusive, such as 0.5%, 0.6%, 0.7%, 0.8%, 0.9%, 1.0%, 1.1%, 1.2%, 1.3%, 1.4%, 1.5%, 1.6%, 1.7%, 1.8%, 1.9%, or 2.0%. In some embodiments, the composition comprises a nutrient that is not an animal product. In some embodiments, the composition comprises a nutrient that is not animal blood. In some embodiments, the composition does not include a nutrient.

In some embodiments of the compositions provided herein, the antioxidant is inulin, riboflavin or cysteine. In some embodiments of the compositions provided herein, the antioxidant is cysteine. In some embodiments of the compositions provided herein, the concentration of cysteine is between 0.01% and 0.5%, inclusive, such as 0.01%, 0.02%, 0.03%, 0.04%, 0.05%, 0.06%, 0.07%, 0.08%, 0.09%, 0.10%, 0.11%, 0.12%, 0.13%, 0.14%, 0.15%, 0.16%, 0.17%, 0.18%, 0.19%, 0.20%, 0.21%, 0.22%, 0.23%, 0.24%, 0.25%, 0.26%, 0.27%, 0.28%, 0.29%, 0.30%, 0.31%, 0.32%, 0.33%, 0.34%, 0.35%, 0.36%, 0.37%, 0.38%, 0.39%, 0.40%, 0.41%, 0.42%, 0.43%, 0.44%, 0.45%, 0.46%, 0.47%, 0.48%, 0.49%, or 0.50%.

In some embodiments, an antioxidant other than, or in addition to, cysteine is added to the composition. Antioxidants that can be added to the composition other than, or in addition to, cysteine include inulin, riboflavin, ascorbic acid (vitamin C), tocopherol, tocotrienol, vitamin E, carotenoids, carotene, provitamin A, vitamin A, propyl gallate, tertiary butylhydroquinone, butylated hydroxyanisole, butylated hydroxytoluene, ubiquinol, glutathione, thiols, polyphenol, catechols, titilazad, NXY-059 (disufenton sodium, Cerovive), oxalic acid, phytic acid, tannins, eugenol, lipoic acid, uric acid, coenzyme Q, melatonin, and combinations thereof. In some embodiments, the composition does not include an antioxidant.

In some embodiments of the compositions provided herein, the buffer is a histidine buffer or a tris buffer (Tris(hydroxymethyl)aminomethane; also known as THAM; 2-Amino-2-(hydroxymethyl)-1,3-propanediol; Tromethamine; or Trometamol). In some embodiments of the compositions provided herein, the buffer is a histidine buffer. In some embodiments of the compositions provided herein, the buffer is about pH 7.0, such as 6.7, 6.8, 6.9, 7.0, 7.1, 7.2, or 7.3. In some embodiments of the compositions provided herein, the concentration of the buffer is between 10 mM and 50 mM, inclusive, such as 10 mM, 11 mM, 12 mM, 13 mM, 14 mM, 15 mM, 16 mM, 17 mM, 18 mM, 19 mM, 20 mM, 21 mM, 22 mM, 23 mM, 24 mM, 25 mM, 26 mM, 27 mM, 28 mM, 29 mM, 30 mM, 31 mM, 32 mM, 33 mM, 34 mM, 35 mM, 36 mM, 37 mM, 38 mM, 39 mM, 40 mM, 41 mM, 42 mM, 43 mM, 44 mM, 45 mM, 46 mM, 47 mM, 48 mM, 49 mM, or 50 mM. In some embodiments, the composition does not include a buffer.

In some embodiments of the compositions provided herein, the composition includes an excipient. In some embodiments, the excipient is a stabilizing agent. In some embodiments of the compositions provided herein, the stabilizing agent is a reducing agent, chelating agent, acid amino acid, basic amino acid, or neutral surfactant, or polymer. In some embodiments, the excipient is a stabilizing agent. In some embodiments of the compositions provided herein, the stabilizing agent is present in the composition at a concentration between 0.01% and 0.1%, inclusive, such as 0.01%, 0.02%, 0.03%, 0.04%, 0.05%, 0.06%, 0.07%, 0.08%, 0.09%, or 0.1%. In some embodiments, the composition does not include an excipient.

In some embodiments, the stabilizing agent is a reducing agent. In some embodiments, the reducing agent is sodium metabisulfite. In some embodiments, the composition comprises sodium metabisulfite between 0.01% and 0.1%, inclusive, such as 0.01%, 0.02%, 0.03%, 0.04%, 0.05%, 0.06%, 0.07%, 0.08%, 0.09%, or 0.1%. In some embodiments, the composition comprises sodium metabisulfite at 0.05%.

In some embodiments, the reducing agent is ascorbic acid. In some embodiments, the reducing agent is citric acid. In some embodiments, the chelating agent is citric acid.

In some embodiments, the stabilizing agent is an acidic amino acid. In some embodiments, the acidic amino acid is sodium glutamate. In some embodiments, the stabilizing agent is a basic amino acid. In some embodiments, the basic amino acid is arginine.

In some embodiments, the stabilizing agent is a neutral surfactant. In some embodiments, the neutral surfactant is polaxamer. In some embodiments, the stabilizing agent is a polymer. In some embodiments, the polymer is nonionic triblock copolymer. In some embodiments, the polymer is polaxamer. In some embodiments, the polymer is polyvinylpyrrolidone (e.g., KOLLIDON®).

In some embodiments, the excipient is not a polymer.

In some embodiments of the compositions provided herein, the composition has been reduced. Methods for reducing a composition are known in the art and include bringing the composition into an anaerobic environment and exposing the composition to the mixed gas atmosphere in the anaerobic chamber.

In some embodiments of the compositions provided herein, the composition includes sucrose, yeast extract, cysteine, and a histidine buffer. In some embodiments of the compositions provided herein, the composition includes sucrose at a concentration between 7.0% and 8.0%, 1% yeast extract, 0.05% cysteine, and 20 mM histidine buffer. In some embodiments of the compositions provided herein, the composition comprises 7.0% sucrose, 1% yeast extract, 0.05% cysteine, and 20 mM histidine buffer. In some embodiments, the composition also includes a bacterial strain. In some embodiments, the bacterial strain is an anaerobic bacterial strain.

In some embodiments of the compositions provided herein, the composition includes sucrose, yeast extract, cysteine, a histidine buffer, and an excipient. In some embodiments of the compositions provided herein, the composition includes sucrose at a concentration between 7.0% and 8.0%, 1% yeast extract, 0.05% cysteine, 20 mM histidine buffer, and 0.05% sodium metabisulfite. In some embodiments of the compositions provided herein, the composition comprises 7.0% sucrose, 1% yeast extract, 0.05% cysteine, 20 mM histidine buffer, and 0.05% sodium metabisulfite. In some embodiments, the composition also includes a bacterial strain. In some embodiments, the bacterial strain is an anaerobic bacterial strain. In some embodiments, the bacterial strain belongs to the class Clostridia.

In some embodiments of the compositions provided herein, the composition includes trehalose, yeast extract, cysteine, and a histidine buffer. In some embodiments of the compositions provided herein, the composition includes trehalose at a concentration between 7.0% and 8.0%, 1% yeast extract, 0.05% cysteine, and 20 mM histidine buffer. In some embodiments of the compositions provided herein, the composition includes 7.5% trehalose, 1% yeast extract, 0.05% cysteine, and 20 mM histidine buffer. In some embodiments, the composition also includes a bacterial strain. In some embodiments, the bacterial strain is an anaerobic bacterial strain.

In some embodiments of the compositions provided herein, the composition includes trehalose, yeast extract, cysteine, a histidine buffer, and an excipient. In some embodiments of the compositions provided herein, the composition includes trehalose at a concentration between 7.0% and 8.0%, 1% yeast extract, 0.05% cysteine, 20 mM histidine buffer, and 0.05% sodium metabisulfite. In some embodiments of the compositions provided herein, the composition includes 7.5% trehalose, 1% yeast extract, 0.05% cysteine, 20 mM histidine buffer, and 0.05% sodium metabisulfite. In some embodiments, the composition also includes a bacterial strain. In some embodiments, the bacterial strain is an anaerobic bacterial strain.

In one aspect, the compositions provided herein allow for preservation of bacteria. The compositions allow the bacteria to go through a freeze-dry cycle with a minimal loss to viability. In some embodiments of the compositions provided herein, the composition includes bacteria. In some embodiments, the composition includes one or more bacterial strains. In some embodiments of the compositions provided herein, the bacteria are anaerobic bacteria (e.g., strict anaerobic bacteria). In some embodiments of the compositions provided herein, the anaerobic bacteria are strict anaerobic bacteria. In some embodiments of the compositions provided herein, the bacteria are from the class Clostridia. In some embodiments of the compositions provided herein, the bacteria are from the family Clostridiaceae. In some embodiments of the compositions provided herein, the bacteria are from the genus *Clostridium*. In some embodiments of the compositions provided herein, the bacteria belong to *Clostridium* cluster IV, XIVa, XVI, XVII, or XVIII. In some embodiments of the compositions provided herein, the bacteria belong to *Clostridium* cluster IV, XIVa, or XVII. In some embodiments of the compositions provided herein, the bacteria belong to *Clostridium* cluster IV or XIVa.

In some embodiments of the compositions provided herein, the composition includes one or more of the following bacterial strains: *Clostridium bolteae, Anaerotruncus colihominis, Eubacterium fissicatena, Clostridium symbiosum, Blautia producta, Dorea longicatena, Erysipelotrichaceae bacterium* and *Subdolinogranulum* spp. In some embodiments of the compositions provided herein, the composition includes one or more of the following bacterial strains: *Clostridium bolteae* 90A9, *Anaerotruncus colihominis* DSM17241, *Sellimonas intestinalis, Clostridium bacterium* UC5.1-1D4, *Dorea longicatena* CAG:42, *Erysipelotrichaceae bacterium* 21-3, and *Clostridium orbiscindens* 1_3_50 AFAA In some embodiments of the compositions provided herein, the composition includes two or more (e.g., 2, 3, 4, 5 6, 7, or 8) of the following bacterial strains: *Clostridium bolteae, Anaerotruncus colihominis, Eubacterium fissicatena, Clostridium symbiosum, Blautia producta, Dorea longicatena, Erysipelotrichaceae bacterium* and *Subdolinogranulum* spp. In some embodiments, the composition includes *Clostridium bolteae*. In some embodiments, the composition includes *Anaerotruncus colihominis*. In some embodiments, the composition includes *Eubacterium fissicatena*. In some embodiments, the composition includes *Clostridium symbiosum*. In some embodiments, the composition includes *Blautia producta*.

In some embodiments, the composition includes *Dorea longicatena*. In some embodiments, the composition includes *Erysipelotrichaceae bacterium*. In some embodiments, the composition includes *Subdolinogranulum* spp.

In one aspect, as shown herein (e.g., in the Examples) the compositions and methods provided herein allow for the stabilization and preservation of anaerobic bacterial strains. In one aspect, as shown herein (e.g., in the Examples) the compositions and methods provided herein allow for the stabilization and preservation of anaerobic bacterial strains belonging to *Clostridium* cluster IV, XIVa, or XVII. In one aspect, as shown herein (e.g., in the Examples) the compositions and methods provided herein allow for the stabilization and preservation of anaerobic bacterial strains *Clostridium bolteae, Anaerotruncus colihominis, Eubacterium fissicatena, Clostridium symbiosum, Blautia producta, Dorea longicatena, Erysipelotrichaceae bacterium* and *Subdolinogranulum* spp. The exemplary bacterial strains of compositions disclosed herein can also be identified by their 16s rRNA sequences (SEQ ID NOs: 1-8). Identifying bacteria by their sequences furthermore allows for the identification of additional bacterial strains that are identical or highly similar to the exemplified bacteria. For instance, the 16s rRNA sequences of bacterial strains were used to identify the closest relative (based on percent identity) through whole genome sequencing and by comparing these sequences with 16S databases (Table 1). In addition, based on whole genome sequencing and comparing of the whole genome to whole genome databases, the bacterial strains having 16S rRNA sequences provided by SEQ ID NOs: 1-8 are most closely related to the following bacterial species: *Clostridium bolteae* 90A9, *Anaerotruncus colihominis* DSM 17241, *Dracourtella massiliensis* GD1, *Clostridium symbiosum* WAL-14163, *Clostridium bacterium* UC5.1-1D4, *Dorea longicatena* CAG:42, *Erysipelotrichaceae bacterium* 21_3, and *Clostridium orbiscindens* 1_3_50 AFAA (see, e.g., Table 1). Thus, in one aspect it should be appreciated that each row of Table 1, the bacterial strains are highly similar and/or are identical. In some embodiments, in context of the instant disclosure the names of bacterial strains within a row of Table 1 can be used interchangeably.

TABLE 1

Examples of Bacterial species of the compositions disclosed herein

| Strain number | SEQ ID NO: | Closest species based on Sanger sequencing of 16S region | Closest species based on Consensus SEQ ID # of 16S region as compared with 16S database | Closest species based on WGS compared versus WG databases | Additional closely related sequences | *Clostridium* cluster |
|---|---|---|---|---|---|---|
| 1 | 1 | *Clostridium bolteae* | *Clostridium bolteae* | *Clostridium bolteae* 90A9 | | XIVa |
| 2 | 2 | *Anaerotruncus colihominis* | *Anaerotruncus colihominis* | *Anaerotruncus colihominis* DSM 17241 | | IV |
| 3 | 3 | *Eubacterium fissicatena* | *Dracourtella massiliensis* | *Dracourtella massiliensis* GD1 | *Ruminococcus torques*; *Sellimonas intestinalis* | XIVa |
| 4 | 4 | *Clostridium symbiosum* | *Clostridium symbiosum* | *Clostridium symbiosum* WAL-14163 | | XIVa |
| 5 | 5 | *Blautia producta* | *Blautia producta* | *Clostridium bacterium* UC5.1-1D4 | *Blautia* product ATCC 27340 | XIVa |
| 6 | 6 | *Dorea longicatena* | *Dorea longicatena* | *Dorea longicatena* CAG:42 | | XIVa |
| 7 | 7 | *Clostridium innocuum* | *Clostridium innocuum* | Erysipelotrichaceae bacterium 21_3 | | XVII |
| 8 | 8 | *Flavinofractor plautii* | *Flavinofractor plautii* | *Clostridium orbiscindens* 1_3_50AFAA | *Subdolinogranulum* | IV |

In some embodiments, the composition includes 7.5% trehalose, 1% yeast extract, 0.05% cysteine, 20 mM histidine buffer, and *Clostridium bolteae*. In some embodiments, the composition includes 7.5% trehalose, 1% yeast extract, 0.05% cysteine, 20 mM histidine buffer, and *Anaerotruncus colihominis*. In some embodiments, the composition includes 7.5% trehalose, 1% yeast extract, 0.05% cysteine, 20 mM histidine buffer, and *Eubacterium fissicatena*. In some embodiments, the composition includes 7.5% trehalose, 1% yeast extract, 0.05% cysteine, 20 mM histidine buffer, and *Clostridium symbiosum*. In some embodiments, the composition includes 7.5% trehalose, 1% yeast extract, 0.05% cysteine, 20 mM histidine buffer, and *Blautia producta*. In some embodiments, the composition includes 7.5% trehalose, 1% yeast extract, 0.05% cysteine, 20 mM histidine buffer, and *Dorea longicatena*. In some embodiments, the composition includes 7.5% trehalose, 1% yeast extract, 0.05% cysteine, 20 mM histidine buffer, and *Erysipelotrichaceae bacterium*. In some embodiments, the composition includes 7.5% trehalose, 1% yeast extract, 0.05% cysteine, 20 mM histidine buffer and *Subdolinogranulum* spp.

In some embodiments, the composition includes 7.5% trehalose, 1% yeast extract, 0.05% cysteine, 20 mM histidine buffer, 0.05% sodium metabisulfite, and *Clostridium bolteae*. In some embodiments, the composition includes 7.5% trehalose, 1% yeast extract, 0.05% cysteine, 20 mM histidine buffer, 0.05% sodium metabisulfite, and *Anaerotruncus colihominis*. In some embodiments, the composition includes 7.5% trehalose, 1% yeast extract, 0.05% cysteine, 20 mM histidine buffer, 0.05% sodium metabisulfite, and *Eubacterium fissicatena*. In some embodiments, the composition includes 7.5% trehalose, 1% yeast extract, 0.05% cysteine, 20 mM histidine buffer, 0.05% sodium metabisulfite, and *Clostridium symbiosum*. In some embodiments, the composition includes 7.5% trehalose, 1% yeast extract, 0.05% cysteine, 20 mM histidine buffer, 0.05% sodium metabisulfite, and *Blautia producta*. In some embodiments, the composition includes 7.5% trehalose, 1% yeast extract, 0.05% cysteine, 20 mM histidine buffer, 0.05% sodium metabisulfite, and *Dorea longicatena*. In some embodiments, the composition includes 7.5% trehalose, 1% yeast extract, 0.05% cysteine, 20 mM histidine buffer and *Erysipelotrichaceae bacterium*. In some embodiments, the composition includes 7.5% trehalose, 1% yeast extract, 0.05% cysteine, 20 mM histidine buffer, 0.05% sodium metabisulfite, and *Subdolinogranulum* spp.

In some embodiments, the composition includes 7.0% sucrose, 1% yeast extract, 0.05% cysteine, 20 mM histidine buffer, and *Clostridium bolteae*. In some embodiments, the composition includes 7.0% sucrose, 1% yeast extract, 0.05% cysteine, 20 mM histidine buffer, and *Anaerotruncus colihominis*. In some embodiments, the composition includes 7.0% sucrose, 1% yeast extract, 0.05% cysteine, 20 mM histidine buffer, and *Eubacterium fissicatena*. In some embodiments, the composition includes 7.0% sucrose, 1% yeast extract, 0.05% cysteine, 20 mM histidine buffer, and *Clostridium symbiosum*. In some embodiments, the composition includes 7.0% sucrose, 1% yeast extract, 0.05% cysteine, 20 mM histidine buffer, and *Blautia producta*. In some embodiments, the composition includes 7.0% sucrose, 1% yeast extract, 0.05% cysteine, 20 mM histidine buffer, and *Dorea longicatena*. In some embodiments, the composition includes 7.0% sucrose, 1% yeast extract, 0.05% cysteine, 20 mM histidine buffer, and *Erysipelotrichaceae bacterium*. In some embodiments, the composition includes 7.0% sucrose, 1% yeast extract, 0.05% cysteine, 20 mM histidine buffer, and *Subdolinogranulum* spp.

In some embodiments, the composition includes 7.0% sucrose, 1% yeast extract, 0.05% cysteine, 20 mM histidine buffer, 0.05% sodium metabisulfite, and *Clostridium bolteae*. In some embodiments, the composition includes 7.0% sucrose, 1% yeast extract, 0.05% cysteine, 20 mM histidine buffer, 0.05% sodium metabisulfite, and *Anaerotruncus colihominis*. In some embodiments, the composition includes 7.0% sucrose, 1% yeast extract, 0.05% cysteine, 20 mM histidine buffer, 0.05% sodium metabisulfite, and *Eubacterium fissicatena*. In some embodiments, the composition includes 7.0% sucrose, 1% yeast extract, 0.05% cysteine, 20 mM histidine buffer, 0.05% sodium metabisulfite, and *Clostridium symbiosum*. In some embodiments, the composition includes 7.0% sucrose, 1% yeast extract, 0.05% cysteine, 20 mM histidine buffer, 0.05% sodium metabisulfite, and *Blautia producta*. In some embodiments, the composition includes 7.0% sucrose, 1% yeast extract, 0.05% cysteine, 20 mM histidine buffer, 0.05% sodium metabisulfite, and *Dorea longicatena*. In some embodiments, the composition includes 7.0% sucrose, 1% yeast extract, 0.05% cysteine, 20 mM histidine buffer, 0.05% sodium metabisulfite, and *Erysipelotrichaceae bacterium*. In some embodiments, the composition includes 7.0% sucrose, 1% yeast extract, 0.05% cysteine, 20 mM histidine buffer, 0.05% sodium metabisulfite, and *Subdolinogranulum* spp.

Aspects of the disclosure relate to bacterial strains with 16S rDNA sequences that have homology to a nucleic acid sequence of any one of the sequences of the bacterial strains or species described herein. In some embodiments, the bacterial strain has at least 80%, 81%, 82%, 83%, 84%, 85%, 86%, 87%, 88%, 89%, 90%, 91%, 92%, 93%, 94%, 95%, 96%, 97%, 98%, 99%, 99.5%, 99.6%, 99.7%, 99.8% or 99.9% homology relative to any of the strains or bacterial species described herein over a specified region of nucleic acid or amino acid sequence or over the entire sequence. It would be appreciated by one of skill in the art that the term "homology" or "percent homology," in the context of two or more nucleic acid sequences or amino acid sequences, refers to a measure of similarity between two or more sequences or portion(s) thereof. The homology may exist over a region of a sequence that is at least about 50 nucleotides in length, or more preferably over a region that is 100 to 500 or 1000 or more nucleotides in length. In some embodiments, the homology exists over the length the 16S rRNA or 16S rDNA sequence, or a portion thereof.

In some embodiments of the compositions provided herein, the composition includes one or more bacterial strains, wherein the one or more bacterial strains include one or more 16s rDNA sequences having at least 97% homology with nucleic acid sequences of SEQ ID NO:1, SEQ ID NO:2, SEQ ID NO:3, SEQ ID NO:4, SEQ ID NO:5, SEQ ID NO:6, SEQ ID NO:7, or SEQ ID NO:8. In some embodiments of the compositions provided herein, the composition includes one bacterial strain, wherein the bacterial strain includes one or more 16s rDNA sequences having at least 97% homology with nucleic acid sequences SEQ ID NO:1, SEQ ID NO:2, SEQ ID NO:3, SEQ ID NO:4, SEQ ID NO:5, SEQ ID NO:6, SEQ ID NO:7, or SEQ ID NO:8. In some embodiments of the compositions provided herein, the composition includes one bacterial strain, wherein the bacterial strain includes one or more 16s rDNA sequences having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.9%, or up to 100% homology with nucleic acid sequences SEQ ID NO:1, SEQ ID NO:2, SEQ ID NO:3, SEQ ID NO:4, SEQ ID NO:5, SEQ ID NO:6, SEQ ID NO:7, or SEQ ID NO:8.

In some embodiments of the compositions provided herein, the composition includes one bacterial strain, wherein the bacterial strain includes one or more 16s rDNA sequences having at least 97% homology with nucleic acid sequences SEQ ID NO:1. In some embodiments of the compositions provided herein, the composition includes one bacterial strain, wherein the bacterial strain includes one or more 16s rDNA sequences having at least 97% homology with nucleic acid sequences SEQ ID NO:2. In some embodiments of the compositions provided herein, the composition includes one bacterial strain, wherein the bacterial strain includes one or more 16s rDNA sequences having at least 97% homology with nucleic acid sequences SEQ ID NO:3. In some embodiments of the compositions provided herein, the composition includes one bacterial strain, wherein the bacterial strain includes one or more 16s rDNA sequences having at least 97% homology with nucleic acid sequences SEQ ID NO:4. In some embodiments of the compositions provided herein, the composition includes one bacterial strain, wherein the bacterial strain includes one or more 16s rDNA sequences having at least 97% homology with nucleic acid sequences SEQ ID NO:5. In some embodiments of the compositions provided herein, the composition includes one bacterial strain, wherein the bacterial strain includes one or more 16s rDNA sequences having at least 97% homology with nucleic acid sequences SEQ ID NO:6. In some embodiments of the compositions provided herein, the composition includes one bacterial strain, wherein the bacterial strain includes one or more 16s rDNA sequences having at least 97% homology with nucleic acid sequences SEQ ID NO:7. In some embodiments of the compositions provided herein, the composition includes one bacterial strain, wherein the bacterial strain includes one or more 16s rDNA sequences having at least 97% homology with nucleic acid sequences SEQ ID NO:8.

Additionally, or alternatively, two or more sequences may be assessed for the identity between the sequences. The terms "identical," percent "identity" in the context of two or more nucleic acids or amino acid sequences, refer to two or more sequences or subsequences that are the same. Two sequences are "substantially identical" if two sequences have a specified percentage of amino acid residues or nucleotides that are the same (e.g., at least 80%, 85%, 90%, 95%, 96%, 97%, 98%, 99%, 99.5%, 99.6%, 99.7%, 99.8% or 99.9% sequence identity) over a specified region of a nucleic acid or amino acid sequence or over an entire sequence, when compared and aligned for maximum correspondence over a comparison window, or designated region as measured using one of the following sequence comparison algorithms or by manual alignment and visual inspection. Optionally, the identity exists over a region that is at least about 50 nucleotides in length, or more preferably over a region that is 100 to 500 or 1000 or more nucleotides in length. In some embodiments, the identity exists over the length the 16S rRNA or 16S rDNA sequence.

In some embodiments of the compositions provided herein, the composition includes one or more bacterial strains, wherein the one or more bacterial strains include one or more 16s rDNA sequences having at least 97% sequence identity with nucleic acid sequences of SEQ ID NO: 1, SEQ ID NO: 2, SEQ ID NO: 3, SEQ ID NO: 4, SEQ ID NO: 5, SEQ ID NO: 6, SEQ ID NO: 7, or SEQ ID NO: 8. In some embodiments of the compositions provided herein, the composition includes one bacterial strain, wherein the bacterial strain includes one or more 16s rDNA sequences having at least 97% sequence identity with nucleic acid sequences SEQ ID NO: 1, SEQ ID NO: 2, SEQ ID NO: 3, SEQ ID NO: 4, SEQ ID NO: 5, SEQ ID NO: 6, SEQ ID NO: 7, or SEQ ID NO: 8. In some embodiments of the compositions provided herein, the composition includes one bacterial strain, wherein the bacterial strain includes one or more 16s rDNA sequences having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.9%, or up to 100% sequence identity with nucleic acid sequences SEQ ID NO: 1, SEQ ID NO: 2, SEQ ID NO: 3, SEQ ID NO: 4, SEQ ID NO: 5, SEQ ID NO: 6, SEQ ID NO: 7, or SEQ ID NO: 8.

In some embodiments of the compositions provided herein, the composition includes one bacterial strain, wherein the bacterial strain includes one or more 16s rDNA sequences having at least 97% sequence identity with nucleic acid sequences SEQ ID NO: 1. In some embodiments of the compositions provided herein, the composition includes one bacterial strain, wherein the bacterial strain includes one or more 16s rDNA sequences having at least 97% sequence identity with nucleic acid sequences SEQ ID NO: 2. In some embodiments of the compositions provided herein, the composition includes one bacterial strain, wherein the bacterial strain includes one or more 16s rDNA sequences having at least 97% sequence identity with nucleic acid sequences SEQ ID NO: 3. In some embodiments of the compositions provided herein, the composition includes one bacterial strain, wherein the bacterial strain includes one or more 16s rDNA sequences having at least 97% sequence identity with nucleic acid sequences SEQ ID NO:4. In some embodiments of the compositions provided herein, the composition includes one bacterial strain, wherein the bacterial strain includes one or more 16s rDNA sequences having at least 97% sequence identity with nucleic acid sequences SEQ ID NO:5. In some embodiments of the compositions provided herein, the composition includes one bacterial strain, wherein the bacterial strain includes one or more 16s rDNA sequences having at least 97% sequence identity with nucleic acid sequences SEQ ID NO:6. In some embodiments of the compositions provided herein, the composition includes one bacterial strain, wherein the bacterial strain includes one or more 16s rDNA sequences having at least 97% sequence identity with nucleic acid sequences SEQ ID NO:7. In some embodiments of the compositions provided herein, the composition includes one bacterial strain, wherein the bacterial strain includes one or more 16s rDNA sequences having at least 97% sequence identity with nucleic acid sequences SEQ ID NO:8.

Additionally, or alternatively, two or more sequences may be assessed for the alignment between the sequences. The terms "alignment" or percent "alignment" in the context of two or more nucleic acids or amino acid sequences, refer to two or more sequences or subsequences that are the same. Two sequences are "substantially aligned" if two sequences have a specified percentage of amino acid residues or nucleotides that are the same (e.g., at least 80%, 85%, 90%, 95%, 96%, 97%, 98%, 99%, 99.5%, 99.6%, 99.7%, 99.8% or 99.9% identical) over a specified region of the nucleic acid or amino acid sequence or over the entire sequence, when compared and aligned for maximum correspondence over a comparison window, or designated region as measured using one of the following sequence comparison algorithms or by manual alignment and visual inspection. Optionally, the alignment exists over a region that is at least about 50 nucleotides in length, or more preferably over a region that is 100 to 500 or 1000 or more nucleotides in length. In some embodiments, the identity exists over the length the 16S rRNA or 16S rDNA sequence.

For sequence comparison, typically one sequence acts as a reference sequence, to which test sequences are compared. Methods of alignment of sequences for comparison are well known in the art. See, e.g., by the local homology algorithm of Smith and Waterman (1970) *Adv. Appl. Math.* 2:482c, by the homology alignment algorithm of Needleman and Wunsch, *J. Mol. Biol.* (1970) 48:443, by the search for similarity method of Pearson and Lipman. *Proc. Natl. Acad. Sci. USA* (1998) 85:2444, by computerized implementations of these algorithms (GAP, BESTFIT, FASTA, and TFASTA in the Wisconsin Genetics Software Package, Genetics Computer Group. Madison. Wis.), or by manual alignment and visual inspection (see. e.g., Brent et al., *Current Protocols in Molecular Biology*, John Wiley & Sons, Inc. (Ringbou ed., 2003)). Two examples of algorithms that are suitable for determining percent sequence identity and sequence similarity are the BLAST and BLAST 2.0 algorithms, which are described in Altschul et al., *Nuc. Acids Res.* (1977) 25:3389-3402, and Altschul et al., *J. Mol. Biol.* (1990) 215:403-410, respectively.

It should be appreciated that the terms "bacteria" and "bacterial strains" as used herein are interchangeable.

In some embodiments, the bacterial strains are grown up from a single colony. In some embodiments, the bacterial strains are purified bacterial strains. As used herein, the term "purified" refers to a bacterial strain or composition comprising such that has been separated from one or more components, such as contaminants. In some embodiments, the bacterial strain is substantially free of contaminants. In some embodiments, one or more bacterial strains of a composition may be independently purified from one or more other bacteria produced and/or present in a culture or a sample containing the bacterial strain. In some embodiments, a bacterial strain is isolated or purified from a sample and then cultured under the appropriate conditions for bacterial replication, e.g., under anaerobic culture conditions. The bacteria that is grown under appropriate conditions for bacterial replication can subsequently be isolated/purified from the culture in which it is grown.

The bacterial strains of the composition can be manufactured using fermentation techniques well known in the art. In some embodiments, the active ingredients are manufactured using anaerobic fermenters, which can support the rapid growth of anaerobic bacterial strains. The anaerobic fermenters may be, for example, stirred tank reactors or disposable wave bioreactors. Culture media such as BL media and EG media, or similar versions of these media devoid of animal components, can be used to support the growth of the bacterial species. The bacterial product can be purified and concentrated from the fermentation broth by traditional techniques, such as centrifugation and filtration. Generally, the bacteria are pelleted prior to introducing the bacteria in the composition that already includes the lyoprotectant, nutrient, buffer, and antioxidant. In some embodiments, the bacteria are pelleted prior to introducing the bacteria in the composition that already includes the lyoprotectant, nutrient, buffer, antioxidant, and excipient (e.g., reducing agent).

In some embodiments, the compositions disclosed herein contain about 10, about $10^2$, about $10^3$, about $10^4$, about $10^5$, about $10^6$, about $10^7$, about $10^8$, about $10^9$, about $10^{10}$, about $10^{11}$, about $10^{12}$, about $10^{13}$ or more bacteria. In some embodiments, the compositions disclosed herein contain about 10, about $10^2$, about $10^3$, about $10^4$, about $10^5$, about $10^6$, about $10^7$, about $10^8$, about $10^9$, about $10^{10}$, about $10^{11}$, about $10^{12}$, about $10^{13}$ or more bacteria per milliliter. It should be appreciated that some of the bacteria may not be viable. In some embodiments, the compositions disclosed herein contain about 10, about $10^2$, about $10^3$, about $10^4$, about $10^5$, about $10^6$, about $10^7$, about $10^8$, about $10^9$, about $10^{10}$, about $10^{11}$, about $10^{12}$, about $10^{13}$ or more colony forming units (cfus) of bacteria. In some embodiments, the compositions disclosed herein contain about 10, about $10^2$, about $10^3$, about $10^4$, about $10^5$, about $10^6$, about $10^7$, about $10^8$, about $10^9$, about $10^{10}$, about $10^{11}$, about $10^{12}$, about $10^{13}$ or more colony forming units (cfus) of bacteria per milliliter.

In some embodiments, the compositions disclosed herein contain between 10 and $10^{13}$, between $10^2$ and $10^{13}$, between $10^3$ and $10^{13}$, between $10^4$ and $10^{13}$, between $10^5$ and $10^{13}$, between $10^6$ and $10^{13}$, between $10^7$ and $10^{13}$, between $10^8$ and $10^{13}$, between $10^9$ and $10^{13}$, between $10^{10}$ and $10^{13}$, between $10^{11}$ and $10^{13}$, between $10^{12}$ and $10^{13}$, between 10 and $10^{12}$, between $10^2$ and $10^{12}$, between $10^3$ and $10^{12}$, between $10^4$ and $10^{12}$, between $10^5$ and $10^{12}$, between $10^6$ and $10^{12}$, between $10^7$ and $10^{12}$, between $10^8$ and $10^{12}$, between $10^9$ and $10^{12}$, between $10^{10}$ and $10^{12}$, between $10^{11}$ and $10^{12}$, between $10$ and $10^{11}$, between $10^2$ and $10^{11}$, between $10^3$ and $10^{13}$, between $10^4$ and $10^{13}$, between $10^5$ and $10^{13}$, between $10^6$ and $10^{13}$, between $10^7$ and $10^{11}$, between $10^8$ and $10^{11}$, between $10^9$ and $10^{11}$, between $10^{10}$ and $10^{11}$, between $10$ and $10^{10}$, between $10^2$ and $10^{10}$, between $10^3$ and $10^{10}$, between $10^4$ and $10^{10}$, between $10^5$ and $10^{10}$, between $10^6$ and $10^{10}$, between $10^7$ and $10^{10}$, between $10^8$ and $10^{10}$, between $10^9$ and $10^{10}$, between $10$ and $10^9$, between $10^2$ and $10^9$, between $10^3$ and $10^9$, between $10^4$ and $10^9$, between $10^5$ and $10^9$, between $10^6$ and $10^9$, between $10^7$ and $10^9$, between $10^8$ and $10^9$, between $10$ and $10^8$, between $10^2$ and $10^8$, between $10^3$ and $10^8$, between $10^4$ and $10^8$, between $10^5$ and $10^8$, between $10^6$ and $10^8$, between $10^7$ and $10^8$, between $10$ and $10^7$, between $10^2$ and $10^7$, between $10^3$ and $10^7$, between $10^4$ and $10^7$, between $10^5$ and $10^7$, between $10^6$ and $10^7$, between $10$ and $10^6$, between $10^2$ and $10^6$, between $10^3$ and $10^6$, between $10^4$ and $10^6$, between $10^5$ and $10^6$, between $10$ and $10^5$, between $10^2$ and $10^5$, between $10^3$ and $10^5$, between $10^4$ and $10^5$, between $10$ and $10^4$, between $10^2$ and $10^4$, between $10^3$ and $10^4$, between $10$ and $10^3$, between $10^2$ and $10^3$, or between $10$ and $10^2$ total bacteria. In some embodiments, the compositions disclosed herein contain between $10$ and $10^{13}$, between $10^2$ and $10^{13}$, between $10^3$ and $10^{13}$, between $10^4$ and $10^{13}$, between $10^5$ and $10^{13}$, between $10^6$ and $10^{13}$, between $10^7$ and $10^{13}$, between $10^8$ and $10^{13}$, between $10^9$ and $10^{13}$, between $10^{10}$ and $10^{13}$, between $10^{11}$ and $10^{13}$, between $10^{12}$ and $10^{13}$, between $10$ and $10^{12}$, between $10^2$ and $10^{12}$, between $10^3$ and $10^{12}$, between $10^4$ and $10^{12}$, between $10^5$ and $10^{12}$, between $10^6$ and $10^{12}$, between $10^7$ and $10^{12}$, between $10^8$ and $10^{12}$, between $10^9$ and $10^{12}$, between $10^{10}$ and $10^{12}$, between $10^{11}$ and $10^{12}$, between $10$ and $10^{11}$, between $10^2$ and $10^{11}$, between $10^3$ and $10^{13}$, between $10^4$ and $10^{13}$, between $10^5$ and $10^{13}$, between $10^6$ and $10^{13}$, between $10^7$ and $10^{11}$, between $10^8$ and $10^{11}$, between $10^9$ and $10^{11}$, between $10^{10}$ and $10^{11}$, between $10$ and $10^{10}$, between $10^2$ and $10^{10}$, between $10^3$ and $10^{10}$, between $10^4$ and $10^{10}$, between $10^5$ and $10^{10}$, between $10^6$ and $10^{10}$, between $10^7$ and $10^{10}$, between $10^8$ and $10^{10}$, between $10^9$ and $10^{10}$, between $10$ and $10^9$, between $10^2$ and $10^9$, between $10^3$ and $10^9$, between $10^4$ and $10^9$, between $10^5$ and $10^9$, between $10^6$ and $10^9$, between $10^7$ and $10^9$, between $10^8$ and $10^9$, between $10$ and $10^8$, between $10^2$ and $10^8$, between $10^3$ and $10^8$, between $10^4$ and $10^8$, between $10^5$ and $10^8$, between $10^6$ and $10^8$, between $10^7$ and $10^8$, between $10$ and $10^7$, between $10^2$ and $10^7$, between $10^3$ and $10^7$, between $10^4$ and $10^7$, between $10^5$ and $10^7$, between $10^6$ and $10^7$, between $10$ and $10^6$, between $10^2$ and $10^6$, between $10^3$ and $10^6$, between $10^4$ and $10^6$, between $10^5$ and $10^6$, between $10$ and $10^5$, between $10^2$ and $10^5$, between $10^3$ and $10^5$, between $10^4$ and $10^5$, between $10$ and $10^4$, between $10^2$ and $10^4$, between $10^3$ and $10^4$, between $10$ and $10^3$, between $10^2$ and $10^3$, or between $10$ and $10^2$ total bacteria per milliliter.

In some embodiments, the compositions disclosed herein contain between $10$ and $10^{13}$, between $10^2$ and $10^{13}$, between $10^3$ and $10^{13}$, between $10^4$ and $10^{13}$, between $10^5$ and $10^{13}$, between $10^6$ and $10^{13}$, between $10^7$ and $10^{13}$, between $10^8$ and $10^{13}$, between $10^9$ and $10^{13}$, between $10^{10}$ and $10^{13}$, between $10^{11}$ and $10^{13}$, between $10^{12}$ and $10^{13}$, between $10$ and $10^{12}$, between $10^2$ and $10^{12}$, between $10^3$ and $10^{12}$, between $10^4$ and $10^{12}$, between $10^5$ and $10^{12}$, between $10^6$ and $10^{12}$, between $10^7$ and $10^{12}$, between $10^8$ and $10^{12}$, between $10^9$ and $10^{12}$, between $10^{10}$ and $10^{12}$, between $10^{11}$ and $10^{12}$, between $10$ and $10^{11}$, between $10^2$ and $10^{11}$, between $10^3$ and $10^{13}$, between $10^4$ and $10^{13}$, between $10^5$ and $10^{13}$, between $10^6$ and $10^{13}$, between $10^7$ and $10^{11}$, between $10^8$ and $10^{11}$, between $10^9$ and $10^{11}$, between $10^{10}$ and $10^{11}$, between $10$ and $10^{10}$, between $10^2$ and $10^{10}$, between $10^3$ and $10^{10}$, between $10^4$ and $10^{10}$, between $10^5$ and $10^{10}$, between $10^6$ and $10^{10}$, between $10^7$ and $10^{10}$, between $10^8$ and $10^{10}$, between $10^9$ and $10^{10}$, between $10$ and $10^9$, between $10^2$ and $10^9$, between $10^3$ and $10^9$, between $10^4$ and $10^9$, between $10^5$ and $10^9$, between $10^6$ and $10^9$, between $10^7$ and $10^9$, between $10^8$ and $10^9$, between $10$ and $10^8$, between $10^2$ and $10^8$, between $10^3$ and $10^8$, between $10^4$ and $10^8$, between $10^5$ and $10^8$, between $10^6$ and $10^8$, between $10^7$ and $10^8$, between $10$ and $10^7$, between $10^2$ and $10^7$, between $10^3$ and $10^7$, between $10^4$ and $10^7$, between $10^5$ and $10^7$, between $10^6$ and $10^7$, between $10$ and $10^6$, between $10^2$ and $10^6$, between $10^3$ and $10^6$, between $10^4$ and $10^6$, between $10^5$ and $10^6$, between $10$ and $10^5$, between $10^2$ and $10^5$, between $10^3$ and $10^5$, between $10^4$ and $10^5$, between $10$ and $10^4$, between $10^2$ and $10^4$, between $10^3$ and $10^4$, between $10$ and $10^3$, between $10^2$ and $10^3$, or between $10$ and $10^2$ colony forming units of bacteria. In some embodiments, the compositions disclosed herein contain between $10$ and $10^{13}$, between $10^2$ and $10^{13}$, between $10^3$ and $10^{13}$, between $10^4$ and $10^{13}$, between $10^5$ and $10^{13}$, between $10^6$ and $10^{13}$, between $10^7$ and $10^{13}$, between $10^8$ and $10^{13}$, between $10^9$ and $10^{13}$, between $10^{10}$ and $10^{13}$, between $10^{11}$ and $10^{13}$, between $10^{12}$ and $10^{13}$, between $10$ and $10^{12}$, between $10^2$ and $10^{12}$, between $10^3$ and $10^{12}$, between $10^4$ and $10^{12}$, between $10^5$ and $10^{12}$, between $10^6$ and $10^{12}$, between $10^7$ and $10^{12}$, between $10^8$ and $10^{12}$, between $10^9$ and $10^{12}$, between $10^{10}$ and $10^{12}$, between $10^{11}$ and $10^{12}$, between $10$ and $10^{11}$, between $10^2$ and $10^{11}$, between $10^3$ and $10^{13}$, between $10^4$ and $10^{13}$, between $10^5$ and $10^{13}$, between $10^6$ and $10^{13}$, between $10^7$ and $10^{11}$, between $10^8$ and $10^{11}$, between $10^9$ and $10^{11}$, between $10^{10}$ and $10^{11}$, between $10$ and $10^{10}$, between $10^2$ and $10^{10}$, between $10^3$ and $10^{10}$, between $10^4$ and $10^{10}$, between $10^5$ and $10^{10}$, between $10^6$ and $10^{10}$, between $10^7$ and $10^{10}$, between $10^8$ and $10^{10}$, between $10^9$ and $10^{10}$, between $10$ and $10^9$, between $10^2$ and $10^9$, between $10^3$ and $10^9$, between $10^4$ and $10^9$, between $10^5$ and $10^9$, between $10^6$ and $10^9$, between $10^7$ and $10^9$, between $10^8$ and $10^9$, between $10$ and $10^8$, between $10^2$ and $10^8$, between $10^3$ and $10^8$, between $10^4$ and $10^8$, between $10^5$ and $10^8$, between $10^6$ and $10^8$, between $10^7$ and $10^8$, between $10$ and $10^7$, between $10^2$ and $10^7$, between $10^3$ and $10^7$, between $10^4$ and $10^7$, between $10^5$ and $10^7$, between $10^6$ and $10^7$, between $10$ and $10^6$, between $10^2$ and $10^6$, between $10^3$ and $10^6$, between $10^4$ and $10^6$, between $10^5$ and $10^6$, between $10$ and $10^5$, between $10^2$ and $10^5$, between $10^3$ and $10^5$, between $10^4$ and $10^5$, between $10$ and $10^4$, between $10^2$ and $10^4$, between $10^3$ and $10^4$, between $10$ and $10^3$, between $10^2$ and $10^3$, or between $10$ and $10^2$ colony forming units of bacteria per milliliter.

In some embodiments of the compositions provided herein, the composition includes at least $1 \times 10^8$ colony forming units of bacteria per milliliter.

Compositions that include bacterial strains can be lyophilized to preserve the bacterial strain. In some embodiments, the composition or the bacterial strains of the composition are lyophilized. Methods of lyophilizing compositions, including compositions comprising bacteria, are known in the art. See, e.g., U.S. Pat. Nos. 3,261,761; 4,205,132; PCT Publications WO 2014/029578, WO 2012/098358, WO2012/076665 and WO2012/088261, herein incorporated by reference in their entirety. However, finding conditions that allow for the lyophilization of certain bacteria, such as anaerobic bacteria has been challenging. See e.g., Peiren et al., Appl Microbol Biotechnol (2015) 99: 3559. It should be appreciated that in one aspect the methods of stabilization and preservation provided herein allow for the ability to generate compositions that allow for the manufacture of bacterial strains, in particular anaerobic bacterial strains. Prior to the instant disclosure, none of the published methods provided for levels of stabilization and preservation that would allow for the manufacture of bacterial strains, particular anaerobic bacterial strains.

Aspects of the disclosure provide methods of preserving bacteria involving subjecting a composition comprising the bacteria to a lyphophilization cycle. In general, lyophilization is a dessication process to preserve a material, such as bacteria, involving freeze-drying. Water is removed from material by freezing the material and then placing the material under a vacuum, during which the ice undergoes sublimation. In some embodiments, the lyophilization cycle involves the steps of freezing, primary drying, and secondary drying. The term "temperature ramp rate" refers to the rate by which the temperature is adjusted between steps of the lyophilization cycle.

In some embodiments, the lyophilization cycle includes one or more steps having a temperature ramp rate between 0.5° C./min to 3° C./min. In some embodiments, the temperature ramp rate is 0.5° C./min, 0.6° C./min, 0.7° C./min, 0.8° C./min, 0.9° C./min, 1.0° C./min, 1.1° C./min, 1.2° C./min, 1.3° C./min, 1.4° C./min, 1.5° C./min, 1.6° C./min, 1.7° C./min, 1.8° C./min, 1.9° C./min, 2.0° C./min, 2.1° C./min, 2.2° C./min, 2.3° C./min, 2.4° C./min, 2.5° C./min, 2.6° C./min, 2.7° C./min, 2.8° C./min, 2.9° C./min, or 3.0° C./min. In some embodiments, the lyophilization cycle includes one or more steps having a temperature ramp rate of 1.0° C./min.

In some embodiments, the lyophilization cycle includes one or more steps having a temperature ramp rate of 2.5° C./min.

In some embodiments, each of the steps of the lyophilization cycle have a temperature ramp rate between 0.5° C./min to 3° C./min. In some embodiments, the temperature ramp rate is 0.5° C./min, 0.6° C./min, 0.7° C./min, 0.8° C./min, 0.9° C./min, 1.0° C./min, 1.1° C./min, 1.2° C./min, 1.3° C./min, 1.4° C./min, 1.5° C./min, 1.6° C./min, 1.7° C./min, 1.8° C./min, 1.9° C./min, 2.0° C./min, 2.1° C./min, 2.2° C./min, 2.3° C./min, 2.4° C./min, 2.5° C./min, 2.6° C./min, 2.7° C./min, 2.8° C./min, 2.9° C./min, or 3.0° C./min. In some embodiments, each of the steps of the lyophilization cycle have a temperature ramp rate of 1.0° C./min. In some embodiments, each of the steps of the lyophilization cycle have a temperature ramp rate of 2.5° C./min.

As discussed herein, in some embodiments, a bacteria may be determined to be sensitive, for example in a sensitivity assay, and the temperature ramp rate in the lyophilization is increased. In some embodiments, a bacteria may be determined to be sensitive and the lyophilization cycle includes one or more steps having a temperature ramp rate of 2.5° C./min.

In one aspect, the compositions provided herein that include bacteria are in solid form. In some embodiments, the solid form is a lyophilized cake (also referred to as a "lyocake"). As used herein, the terms "lyophilization cake" and "lyocake" refer to the solid composition formed by lyophilization of a composition, such as a composition comprising bacteria. The appearance of the lyophilization cake may be evaluated. In embodiments, a lyophilization cake that appears intact and not collapsed is desired.

It should be appreciated that the disclosure embraces solid compositions. The solid compositions may be generated for instance after lyophilization of one of the compositions that include bacteria disclosed herein. The solid form of the composition will have the same components as the liquid formulation used to generate the solid form. Thus, for instance, if a liquid composition included lyoprotectant, a nutrient, an antioxidant, and a buffer and the liquid composition was subject to lyophilization, the lyocake generated would have the same components. The definition of the amount/percentage of each of the components is different when describing the solid formulation. The indicators "mM" and "pH: are not appropriate to describe solid components. However, it should be appreciated that reconstitution of a solid formulation in the same amount of liquid should results in the same composition. In one aspect, the disclosure provides solid compositions that have been generated by the lyophilization of the compositions provided herein.

In some embodiments, the disclosure provides a solid composition that includes bacteria generated by the lyophilization of a liquid composition comprising a lyoprotectant, a nutrient, an antioxidant, and a buffer. In some embodiments, the disclosure provides a solid composition that includes bacteria generated by the lyophilization of a liquid composition comprising a lyoprotectant, a nutrient, an antioxidant, a buffer, and an excipient (e.g., stabilizing agent). In some embodiments, the disclosure provides a solid composition that includes bacteria generated by the lyophilization of a liquid composition comprising sucrose, yeast extract, cysteine, and a histidine buffer. In some embodiments, the disclosure provides a solid composition that includes bacteria generated by the lyophilization of a liquid composition comprising sucrose, yeast extract, cysteine, a histidine buffer, and sodium metabisulfite. In some embodiments, the disclosure provides a solid composition that includes bacteria generated by the lyophilization of a liquid composition comprising trehalose, yeast extract, cysteine, and a histidine buffer. In some embodiments, the disclosure provides a solid composition that includes bacteria generated by the lyophilization of a liquid composition comprising trehalose, yeast extract, cysteine, a histidine buffer, and sodium metabisulfite. In some embodiments, the disclosure provides a lyocake that includes bacteria generated by the lyophilization of a liquid composition comprising sucrose, yeast extract, cysteine, and a histidine buffer. In some embodiments, the disclosure provides a lyocake that includes bacteria generated by the lyophilization of a liquid composition comprising sucrose, yeast extract, cysteine, a histidine buffer, and sodium metabisulfite. In some embodiments, the disclosure provides a lyocake that includes bacteria generated by the lyophilization of a liquid composition comprising trehalose, yeast extract, cysteine, and a histidine buffer. In some embodiments, the disclosure provides a lyocake that includes bacteria generated by the lyophilization of a liquid composition comprising trehalose, yeast extract, cysteine, a histidine buffer, and sodium metabisulfite.

In some embodiments of the compositions provided herein, the composition includes a solid composition generated by the lyophilization of 7.5% trehalose, 1% yeast extract, 0.05% cysteine, 20 mM histidine buffer and *Clostridium bolteae*. In some embodiments of the compositions provided herein, the composition includes a solid composition generated by the lyophilization of 7.5% trehalose, 1% yeast extract, 0.05% cysteine, 20 mM histidine buffer, 0.05% sodium metabisulfite, and *Clostridium bolteae*. In some embodiments, the solid composition is a lyocake.

In some embodiments of the compositions provided herein, the composition includes a solid composition generated by the lyophilization of 7.5% trehalose, 1% yeast extract, 0.05% cysteine, 20 mM histidine buffer and *Anaerotruncus colihominis*. In some embodiments of the compositions provided herein, the composition includes a solid composition generated by the lyophilization of 7.5% trehalose, 1% yeast extract, 0.05% cysteine, 20 mM histidine buffer, 0.05% sodium metabisulfite, and *Anaerotruncus colihominis*. In some embodiments, the solid composition is a lyocake.

In some embodiments of the compositions provided herein, the composition includes a solid composition generated by the lyophilization of 7.5% trehalose, 1% yeast extract, 0.05% cysteine, 20 mM histidine buffer, and *Eubacterium fissicatena*. In some embodiments of the compositions provided herein, the composition includes a solid composition generated by the lyophilization of 7.5% trehalose, 1% yeast extract, 0.05% cysteine, 20 mM histidine buffer, 0.05% sodium metabisulfite, and *Eubacterium fissicatena*. In some embodiments, the solid composition is a lyocake.

In some embodiments of the compositions provided herein, the composition includes a solid composition generated by the lyophilization of 7.5% trehalose, 1% yeast extract, 0.05% cysteine, 20 mM histidine buffer, and *Clostridium symbiosum*. In some embodiments of the compositions provided herein, the composition includes a solid composition generated by the lyophilization of 7.5% trehalose, 1% yeast extract, 0.05% cysteine, 20 mM histidine buffer, 0.05% sodium metabisulfite, and *Clostridium symbiosum*. In some embodiments, the solid composition is a lyocake.

In some embodiments of the compositions provided herein, the composition includes a solid composition generated by the lyophilization of 7.5% trehalose, 1% yeast extract, 0.05% cysteine, 20 mM histidine buffer and *Blautia producta*. In some embodiments of the compositions provided herein, the composition includes a solid composition generated by the lyophilization of 7.5% trehalose, 1% yeast extract, 0.05% cysteine, 20 mM histidine buffer, 0.05% sodium metabisulfite, and *Blautia producta*. In some embodiments, the solid composition is a lyocake.

In some embodiments of the compositions provided herein, the composition includes a solid composition generated by the lyophilization of 7.5% trehalose, 1% yeast extract, 0.05% cysteine, 20 mM histidine buffer and *Dorea longicatena*. In some embodiments of the compositions provided herein, the composition includes a solid composition generated by the lyophilization of 7.5% trehalose, 1% yeast extract, 0.05% cysteine, 20 mM histidine buffer, 0.05% sodium metabisulfite, and *Dorea longicatena*. In some embodiments, the solid composition is a lyocake.

In some embodiments of the compositions provided herein, the composition includes a solid composition generated by the lyophilization of 7.5% trehalose, 1% yeast extract, 0.05% cysteine, 20 mM histidine buffer and *Erysipelotrichaceae bacterium*. In some embodiments of the compositions provided herein, the composition includes a solid composition generated by the lyophilization of 7.5% trehalose, 1% yeast extract, 0.05% cysteine, 20 mM histidine buffer, 0.05% sodium metabisulfite, and *Erysipelotrichaceae bacterium*. In some embodiments, the solid composition is a lyocake.

In some embodiments of the compositions provided herein, the composition includes a solid composition generated by the lyophilization of 7.5% trehalose, 1% yeast extract, 0.05% cysteine, 20 mM histidine buffer and *Subdolinogranulum* spp. In some embodiments of the compositions provided herein, the composition includes a solid composition generated by the lyophilization of 7.5% trehalose, 1% yeast extract, 0.05% cysteine, 20 mM histidine buffer, 0.05% sodium metabisulfite, and *Subdolinogranulum* spp. In some embodiments, the solid composition is a lyocake.

In some embodiments of the compositions provided herein, the composition includes a solid composition generated by the lyophilization of 7.0% sucrose, 1% yeast extract, 0.05% cysteine, 20 mM histidine buffer, and *Clostridium bolteae*. In some embodiments of the compositions provided herein, the composition includes a solid composition generated by the lyophilization of 7.0% sucrose, 1% yeast extract, 0.05% cysteine, 20 mM histidine buffer, 0.05% sodium metabisulfite, and *Clostridium bolteae*. In some embodiments, the solid composition is a lyocake.

In some embodiments of the compositions provided herein, the composition includes a solid composition generated by the lyophilization of 7.0% sucrose, 1% yeast extract, 0.05% cysteine, 20 mM histidine buffer, and *Anaerotruncus colihominis*. In some embodiments of the compositions provided herein, the composition includes a solid composition generated by the lyophilization of 7.0% sucrose, 1% yeast extract, 0.05% cysteine, 20 mM histidine buffer, 0.05% sodium metabisulfite, and *Anaerotruncus colihominis*. In some embodiments, the solid composition is a lyocake.

In some embodiments of the compositions provided herein, the composition includes a solid composition generated by the lyophilization of 7.0% sucrose, 1% yeast extract, 0.05% cysteine, 20 mM histidine buffer, and *Eubacterium fissicatena*. In some embodiments of the compositions provided herein, the composition includes a solid composition generated by the lyophilization of 7.0% sucrose, 1% yeast extract, 0.05% cysteine, 20 mM histidine buffer, 0.05% sodium metabisulfite, and *Eubacterium fissicatena*. In some embodiments, the solid composition is a lyocake.

In some embodiments of the compositions provided herein, the composition includes a solid composition generated by the lyophilization of 7.0% sucrose, 1% yeast extract, 0.05% cysteine, 20 mM histidine buffer, and *Clostridium symbiosum*. In some embodiments of the compositions provided herein, the composition includes a solid composition generated by the lyophilization of 7.0% sucrose, 1% yeast extract, 0.05% cysteine, 20 mM histidine buffer, 0.05% sodium metabisulfite, and *Clostridium symbiosum*. In some embodiments, the solid composition is a lyocake.

In some embodiments of the compositions provided herein, the composition includes a solid composition generated by the lyophilization of 7.0% sucrose, 1% yeast extract, 0.05% cysteine, 20 mM histidine buffer and *Blautia producta*. In some embodiments of the compositions provided herein, the composition includes a solid composition generated by the lyophilization of 7.0% sucrose, 1% yeast extract, 0.05% cysteine, 20 mM histidine buffer, 0.05% sodium metabisulfite, and *Blautia producta*. In some embodiments, the solid composition is a lyocake.

In some embodiments of the compositions provided herein, the composition includes a solid composition generated by the lyophilization of 7.0% sucrose, 1% yeast extract, 0.05% cysteine, 20 mM histidine buffer, and *Dorea longicatena*. In some embodiments of the compositions provided herein, the composition includes a solid composition generated by the lyophilization of 7.0% sucrose, 1% yeast extract, 0.05% cysteine, 20 mM histidine buffer, 0.05% sodium metabisulfite, and *Dorea longicatena*. In some embodiments, the solid composition is a lyocake.

In some embodiments of the compositions provided herein, the composition includes a solid composition generated by the lyophilization of 7.0% sucrose, 1% yeast extract, 0.05% cysteine, 20 mM histidine buffer, and *Erysipelotrichaceae bacterium*. In some embodiments of the compositions provided herein, the composition includes a solid composition generated by the lyophilization of 7.0% sucrose, 1% yeast extract, 0.05% cysteine, 20 mM histidine buffer, 0.05% sodium metabisulfite, and *Erysipelotrichaceae bacterium*. In some embodiments, the solid composition is a lyocake.

In some embodiments of the compositions provided herein, the composition includes a solid composition generated by the lyophilization of 7.0% sucrose, 1% yeast extract, 0.05% cysteine, 20 mM histidine buffer and *Subdolinogranulum* spp. In some embodiments of the compositions provided herein, the composition includes a solid composition generated by the lyophilization of 7.0% sucrose, 1% yeast extract, 0.05% cysteine, 20 mM histidine buffer, 0.05% sodium metabisulfite, and *Subdolinogranulum* spp. In some embodiments, the solid composition is a lyocake.

In some embodiments, the solid compositions that include bacterial strains provided herein may be formulated for administration as a pharmaceutical composition, e.g., by reconstitution of a lyophilized product. The term "pharmaceutical composition" as used herein means a product that results from the mixing or combining of a solid formulation provided herein and one or more pharmaceutically acceptable excipient.

An "acceptable" excipient refers to an excipient that must be compatible with the active ingredient (e.g., the bacterial strain) and not deleterious to the subject to which it is administered. In some embodiments, the pharmaceutically acceptable excipient is selected based on the intended route of administration of the composition, for example a composition for oral or nasal administration may comprise a different pharmaceutically acceptable excipient than a composition for rectal administration. Examples of excipients include sterile water, physiological saline, solvent, a base material, an emulsifier, a suspending agent, a surfactant, a stabilizer, a flavoring agent, an aromatic, an excipient, a vehicle, a preservative, a binder, a diluent, a tonicity adjusting agent, a soothing agent, a bulking agent, a disintegrating agent, a buffer agent, a coating agent, a lubricant, a colorant, a sweetener, a thickening agent, and a solubilizer.

In one aspect, the disclosure provides compositions that allow for the preservation of bacteria. In some embodiments, the bacteria are anaerobic bacteria. Compositions useful for the preservations of bacteria are also referred to herein as stabilizing compositions. A composition that allows for the preservation of bacteria (e.g., anaerobic bacteria) or stabilization of bacteria, as used herein, refers to a composition that promotes the viability of the bacteria therein and allows for the recovery of the bacteria following a lyophilization cycle. The stabilization or preservation functionality of the composition can be assessed by comparing the number of viable bacteria (e.g., colony forming units) at two specific time points (e.g., at day 1 and at day 100). In some embodiments, the stabilization or preservation functionality of the composition is assessed by comparing the number of viable bacteria (e.g., colony forming units) at a first time point to the number of viable bacteria (e.g., colony forming units) at a second time point. If the number of colony forming units is the same or substantially the same at the two time points or over a time period, the composition is a perfect stabilizing composition. A large decrease in the number of colony forming units between two time points or over a time period indicates that the composition is not a good stabilizing composition.

The stabilization functionality of the composition can also be assessed by comparing the number of viable bacteria (e.g., colony forming units) before and after a specific event (e.g., lyophilization or a freeze-thaw event). If the number of colony forming units is the same or substantially the same, the composition is a perfect stabilizing composition. A large decrease in the number of colony forming units after a specific event, relative to prior to the specific event, indicates that the composition is not a good stabilizing composition.

In some embodiments of the compositions provided herein, the composition is a stabilizing composition. In some embodiments, the stabilizing composition includes trehalose, yeast extract, cysteine, and a histidine buffer. In some embodiments, the stabilizing composition includes 7.5% trehalose, 1% yeast extract, 0.05% cysteine, and 20 mM histidine buffer. In some embodiments, the stabilizing composition includes trehalose at a concentration between 7.0% and 8.0%, 1% yeast extract, 0.05% cysteine and 20 mM histidine buffer. In some embodiments, the stabilizing composition includes trehalose, yeast extract, cysteine, a histidine buffer, and an excipient (e.g., a stabilizing agent). In some embodiments, the stabilizing composition includes 7.5% trehalose, 1% yeast extract, 0.05% cysteine, 20 mM histidine buffer, and 0.05% sodium metabisulfite. In some embodiments, the stabilizing composition includes trehalose at a concentration between 7.0% and 8.0%, 1% yeast extract, 0.05% cysteine, 20 mM histidine buffer, and 0.05% sodium metabisulfite.

In some embodiments, the stabilizing composition includes sucrose, yeast extract, cysteine, and a histidine buffer. In some embodiments, the stabilizing composition includes sucrose at a concentration between 7.0% and 8.0%, 1% yeast extract, 0.05% cysteine, and 20 mM histidine buffer. In some embodiments, the stabilizing composition comprises 7.0% sucrose, 1% yeast extract, 0.05% cysteine, and 20 mM histidine buffer. In some embodiments, the stabilizing composition includes sucrose, yeast extract, cysteine, a histidine buffer, and an excipient (e.g., a stabilizing agent). In some embodiments, the stabilizing composition includes sucrose at a concentration between 7.0% and 8.0%, 1% yeast extract, 0.05% cysteine, 20 mM histidine buffer, and 0.05% sodium metabisulfite. In some embodiments, the stabilizing composition comprises 7.0% sucrose, 1% yeast extract, 0.05% cysteine, 20 mM histidine buffer, and 0.05% sodium metabisulfite.

Aspects of the disclosure relate to assessing the bacteria in a sensitivity assay. In some embodiments, the bacteria are subjected to a sensitivity assay prior to adding the bacteria to a composition for lyophilization. Sensitivity assays may be used to determine whether a bacterial may be more sensitive, for example to stresses, such as the presence of oxygen or cell wall/membrane stress. The performance of bacteria in a sensitivity assay may also indicate or predict how the bacteria will survive (remain viable) through a lyophilization cycle. In general, subjecting bacteria that are determined to be sensitive, or more sensitive relative to other bacteria, to a lyophilization cycle may result in reduced recovery of viable bacteria; therefore, in some embodiments, if a bacteria is determined to be sensitive, an excipient may be added to the composition and/or the temperature ramp rate of the lyophilization cycle may be increased. In some embodiments, the sensitivity assay may determine the sensitivity of the bacteria to a stress.

In some embodiments, the sensitivity of a bacteria is compared to the sensitivity of another bacteria or to a reference value. In some embodiments, performance of the bacteria in the sensitivity assay may be compared to the performance of another bacteria or to a reference value. Examples of sensitivity assays include, for example, Gram staining and freeze-thaw assays.

Gram staining is a method typically used to assess the cell wall (peptidoglycan) structure of bacteria. As will be evident to one of ordinary skill in the art, a Gram stain involves subjecting bacteria to a series of steps: first contacting the bacteria with a water-soluble dye (crystal violet) and an iodine solution, then a decolorizing step, and finally a counterstaining step, typically with safanin. The crystal violet binds to peptidoglycan of the bacterial cell wall and forms complexes with the iodine. Bacteria having thick layers of peptidoglycan appear purple in a Gram stain and are referred to as Gram positive (Gram +), whereas bacteria having thinner layers of peptidoglycan or are surrounded with an outer membrane, appear pink in a Gram stain, as these cells are stained with the counterstain and not crystal violet. These cells are referred to as Gram negative (Gram −) bacteria. Bacteria that are characterized as Gram positive (e.g., known in the art to have the peptidoglycan structure of Gram positive bacteria) but do not appear Gram positive in a Gram stain may be considered sensitive or more sensitive compared to other bacteria. In some embodiments, the bacteria are subjected to a Gram stain and are determined to be sensitive.

In some embodiments, the sensitivity assay is a freeze-thaw assay. As will be evident to one of ordinary skill in the art, freeze-thaw assays involve freezing bacteria, e.g. in a dry ice/ethanol bath or freezer, and then thawing the bacteria. In some embodiments, the freeze-thaw assay involves one or more cycles of freezing and thawing the bacteria. In some embodiments, the viability of the bacteria is assessed after the freeze-thaw assay. The freeze-thaw process may cause lysis and therefore reduced viability (reduced recovery) of sensitive bacteria. In some embodiments, reduced viability of bacteria in a freeze-thaw assay may indicated that the bacteria are sensitive or are more sensitive compared to other bacteria. In some embodiments, the methods described herein involve assessing the bacteria in a sensitivity assay. In some embodiments, if the bacteria are determined to be sensitive or more sensitive compared to other bacteria, an excipient is added to compositions containing the sensitive bacteria. In some embodiments, if the bacteria are determined to be sensitive or more sensitive compared to other bacteria, a stabilizing agent is added to compositions containing the sensitive bacteria. In some embodiments, if the bacteria are determined to be sensitive or more sensitive compared to other bacteria, a reducing agent is added to compositions containing the sensitive bacteria. Without wishing to be bound by any particular theory, the presence of a reducing agent may scavenge oxygen in the composition, thereby improving the viability of sensitive bacteria. In some embodiments, if the bacteria are determined to be sensitive or more sensitive compared to other bacteria, 0.05% sodium metabisulfite is added to compositions containing the sensitive bacteria.

In some embodiments, if the bacteria are determined to be sensitive or more sensitive compared to other bacteria, the composition comprising the sensitive bacteria is subjected to a lyophilization cycle having an increased temperature ramp rate (e.g., greater than 1° C./min). Without wishing to be bound by any particular theory, increasing the temperature ramp rate may reduce the potential exposure of the bacteria to oxygen. In some embodiments, if the bacteria are determined to be sensitive or more sensitive compared to other bacteria, lyophilized compositions comprising the sensitive bacteria are generated by subjecting a composition comprising the sensitive bacteria to a lyophilization cycle having one or more steps of a temperature ramp rate of 2.5° C./min.

In some embodiments of the compositions provided herein, a stabilizing composition is a composition that allows for the recovery of at least 1%, at least 10%, at least 20%, at least 30%, at least 40%, at least 50%, at least 60%, at least 70%, at least 80%, at least 90%, up to 100% of the colony forming units over a period of time. In some embodiments, the period of time is at least 1 week, at least 2 weeks, at least 4 weeks, at least 2 months, at least 3 months, at least 6 months, or at least 1 year or more. In some embodiments, the percentage of recovered colony forming units or level of preservation is determined by comparing a number of colony forming units of bacteria (e.g., of a bacterial strain or total bacteria) at a first time point relative to the number of colony forming units of bacteria (e.g., of a bacterial strain or total bacteria) at a second time point over a period of time. For example, a 50% recovery or preservation of 50% of bacteria indicates that half of the bacteria remained viable over the period of time; and a 100% recovery or preservation of 100% of bacteria indicates that all (or substantially all) bacteria remained viable over the period of time.

In some embodiments of the compositions provided herein, a stabilizing composition is a composition that allows for the recovery of at least 1%, at least 10%, at least 20%, at least 30%, at least 40%, at least 50%, at least 60%, at least 70%, at least 80%, at least 90%, up to 100% of the colony forming units after a specific event. In some embodiments, the specific event is a freeze-thaw cycle or a lyophilization cycle. In some embodiments, the percentage of recovered colony forming units or level of preservation is determined by comparing a number of colony forming units of bacteria (e.g., of a bacterial strain or total bacteria) prior to the specific event relative to the number of colony forming units of bacteria (e.g., of a bacterial strain or total bacteria) after the specific event. For example, a 50% recovery or 50% preservation indicates that half of the bacteria remained viable after the specific event; and a 100% recovery or 100% preservation indicates that all (or substantially all) bacteria remained viable after the specific event.

In one aspect, the disclosure provides methods for preserving bacteria. In some embodiments of the methods provided herein, the method includes adding bacteria to any of the compositions provided herein and subjecting the composition to which the bacteria have been added to a lyophilization cycle. In some embodiments of the methods provided herein, the method includes adding bacteria to a composition including sucrose at a concentration between 7.0% and 8.0%, 1% yeast extract, 0.05% cysteine and 20 mM histidine buffer and subjecting the composition to which the bacteria have been added to a lyophilization cycle. In some embodiments of the methods provided herein, the method includes adding bacteria to a composition including sucrose at a concentration between 7.0% and 8.0%, 1% yeast extract, 0.05% cysteine, 20 mM histidine buffer, and 0.05% sodium metabisulfite, and subjecting the composition to which the bacteria have been added to a lyophilization cycle.

In some embodiments of the methods provided herein, the method includes adding bacteria to a composition including trehalose at a concentration between 7.0% and 8.0%, 1% yeast extract, 0.05% cysteine and 20 mM histidine buffer and subjecting the composition to which the bacteria have been added to a lyophilization cycle. In some embodiments of the methods provided herein, the method includes adding bacteria to a composition including trehalose at a concentration between 7.0% and 8.0%, 1% yeast extract, 0.05% cysteine, 20 mM histidine buffer, and 0.05% sodium metabisulfite, and subjecting the composition to which the bacteria have been added to a lyophilization cycle.

In some embodiments of the methods provided herein, the method further includes measuring the number of colony forming units after subjecting the composition comprising the bacteria to the lyophilization cycle. In some embodiments of the methods provided herein, the method results in the preservation of at least 1%, at least 10%, at least 20%, at least 30%, at least 40%, at least 50%, at least 60%, at least 70%, at least 80%, at least 90%, up to 100% of the colony forming units.

In one aspect, the disclosure provides methods for generating the compositions provided herein. In some embodiments of the methods provided herein, the method includes creating a mixture by combining the lyoprotectant, the nutrient, the antioxidant, and the buffer, followed by reduction of the mixture thereby generating the composition. In some embodiments, the method further includes the addition of bacteria.

In some embodiments of the methods provided herein, the method includes creating a mixture by combining trehalose, yeast extract, cysteine and histidine buffer to create a mixture, followed by reduction of the mixture thereby generating the composition. In some embodiments of the methods provided herein, the method includes creating a mixture by combining trehalose, yeast extract, cysteine, histidine buffer, and an excipient to create a mixture, followed by reduction of the mixture thereby generating the composition. In some embodiments of the methods provided herein, the method includes creating a mixture by combining sucrose, yeast extract, cysteine, and histidine buffer to create a mixture, followed by reduction of the mixture thereby generating the composition. In some embodiments of the methods provided herein, the method includes creating a mixture by combining sucrose, yeast extract, cysteine, histidine buffer, and excipient to create a mixture, followed by reduction of the mixture thereby generating the composition.

```
Strain 1 16S ribosomal RNA Clostridium bolteae
                                                       SEQ ID NO: 1
ATGAGAGTTTGATCCTGGCTCAGGATGAACGCTGGCGGCGTGCCTAACACATGCAAGTCGAACGAAGC

AATTAAAATGAAGTTTTCGGATGGATTTTTGATTGACTGAGTGGCGGACGGGTGAGTAACGCGTGGAT

AACCTGCCTCACACTGGGGGATAACAGTTAGAAATGACTGCTAATACCGCATAAGCGCACAGTACCGC

ATGGTACGGTGTGAAAAACTCCGGTGGTGTGAGATGGATCCGCGTCTGATTAGCCAGTTGGCGGGGTA

ACGGCCCACCAAAGCGACGATCAGTAGCCGACCTGAGAGGGTGACCGGCCACATTGGGACTGAGACAC

GGCCCAAACTCCTACGGGAGGCAGCAGTGGGGAATATTGCACAATGGGCGAAAGCCTGATGCAGCGAC

GCCGCGTGAGTGAAGAAGTATTTCGGTATGTAAAGCTCTATCAGCAGGGAAGAAAATGACGGTACCTG

ACTAAGAAGCCCCGGCTAACTACGTGCCAGCAGCCGCGGTAATACGTAGGGGGCAAGCGTTATCCGGA

TTTACTGGGTGTAAAGGGAGCGTAGACGGCGAAGCAAGTCTGAAGTGAAAACCCAGGGCTCAACCCTG

GGACTGCTTTGGAAACTGTTTTGCTAGAGTGTCGGAGAGGTAAGTGGAATTCCTAGTGTAGCGGTGAA

ATGCGTAGATATTAGGAGGAACACCAGTGGCGAAGGCGGCTTACTGGACGATAACTGACGTTGAGGCT

CGAAAGCGTGGGGAGCAAACAGGATTAGATACCCTGGTAGTCCACGCCGTAAACGATGAATGCTAGGT

GTTGGGGGGCAAAGCCCTTCGGTGCCGTCGCAAACGCAGTAAGCATTCCACCTGGGGAGTACGTTCGC

AAGAATGAAACTCAAAGGAATTGACGGGGACCCGCACAAGCGGTGGAGCATGTGGTTTAATTCGAAGC

AACGCGAAGAACCTTACCAAGTCTTGACATCCTCTTGACCGGCGTGTAACGGCGCCTTCCCTTCGGGG

CAAGAGAGACAGGTGGTGCATGGTTGTCGTCAGCTCGTGTCGTGAGATGTTGGGTTAAGTCCCGCAAC

GAGCGCAACCCTTATCCTTAGTAGCCAGCAGGTAAAGCTGGGCACTCTAGGGAGACTGCCAGGGATAA

CCTGGAGGAAGGTGGGGATGACGTCAAATCATCATGCCCCTTATGATTTGGGCTACACACGTGCTACA

ATGGCGTAAACAAAGGGAAGCAAGACAGTGATGTGGAGCAAATCCCAAAAATAACGTCCCAGTTCGGA

CTGTAGTCTGCAACCCGACTACACGAAGCTGGAATCGCTAGTAATCGCGAATCAGAATGTCGCGGTGA

ATACGTTCCCGGGTCTTGTACACACCGCCCGTCACACCATGGGAGTCAGCAACGCCCGAAGTCAGTGA

CCCAACTCGCAAGAGAGGGAGCTGCCGAAGGCGGGGCAGGTAACTGGGGTGAAGTCGTAACAAGGTAG

CCGTATCGGAAGGTGCGGCTGGATCACCTCCTTT
```

-continued

Strain 2 16S ribosomal RNA *Anaerotruncus colihominis*

SEQ ID NO: 2

TCAAAGAGTTTGATCCTGGCTCAGGACGAACGCTGGCGGCGCGCCTAACACATGCAAGTCGAACGGAG
CTTACGTTTTGAAGTTTTCGGATGGATGAATGTAAGCTTAGTGGCGGACGGGTGAGTAACACGTGAGC
AACCTGCCTTTCAGAGGGGGATAACAGCCGGAAACGGCTGCTAATACCGCATGATGTTGCGGGGCAC
ATGCCCCTGCAACCAAAGGAGCAATCCGCTGAAAGATGGGCTCGCGTCCGATTAGCCAGTTGGCGGGG
TAACGGCCCACCAAAGCGACGATCGGTAGCCGGACTGAGAGGTTGAACGGCCACATTGGGACTGAGAC
ACGGCCCAGACTCCTACGGGAGGCAGCAGTGGGGATATTGCACAATGGGCGAAAGCCTGATGCAGCG
ACGCCGCGTGAGGGAAGACGGTCTTCGGATTGTAAACCTCTGTCTTTGGGGAAGAAAATGACGGTACC
CAAAGAGGAAGCTCCGGCTAACTACGTGCCAGCAGCCGCGGTAATACGTAGGGAGCAAGCGTTGTCCG
GAATTACTGGGTGTAAAGGGAGCGTAGGCGGATGGCAAGTAGAATGTTAAATCCATCGGCTCAACCG
GTGGCTGCGTTCTAAACTGCCGTTCTTGAGTGAAGTAGAGGCAGGCGGAATTCCTAGTGTAGCGGTGA
AATGCGTAGATATTAGGAGGAACACCAGTGGCGAAGGCGGCCTGCTGGGCTTTAACTGACGCTGAGGC
TCGAAAGCGTGGGGAGCAAACAGGATTAGATACCCTGGTAGTCCACGCCGTAAACGATGATTACTAGG
TGTGGGGGGACTGACCCCTTCCGTGCCGCAGTTAACACAATAAGTAATCCACCTGGGGAGTACGGCCG
CAAGGTTGAAACTCAAAGGAATTGACGGGGCCCGCACAAGCAGTGGAGTATGTGGTTTAATTCGAAG
CAACGCGAAGAACCTTACCAGGTCTTGACATCGGATGCATAGCCTAGAGATAGGTGAAGCCCTTCGGG
GCATCCAGACAGGTGGTGCATGGTTGTCGTCAGCTCGTGTCGTGAGATGTTGGGTTAAGTCCCGCAAC
GAGCGCAACCCTTATTATTAGTTGCTACGCAAGAGCACTCTAATGAGACTGCCGTTGACAAAACGGAG
GAAGGTGGGGATGACGTCAAATCATCATGCCCCTTATGACCTGGGCTACACACGTACTACAATGGCAC
TAAAACAGAGGGCGGCGACACCGCGAGGTGAAGCGAATCCCGAAAAAGTGTCTCAGTTCAGATTGCAG
GCTGCAACCCGCCTGCATGAAGTCGGAATTGCTAGTAATCGCGGATCAGCATGCCGCGGTGAATACGT
TCCCGGGCCTTGTACACACCGCCCGTCACACCATGGGAGTCGGTAACACCCGAAGCCAGTAGCCTAAC
CGCAAGGGGGCGCTGTCGAAGGTGGGATTGATGACTGGGGTGAAGTCGTAACAAGGTAGCCGTATCG
GAAGGTGCGGCTGGATCACCTCCTTT

Strain 3 16S ribosomal RNA *Ruminococcus torques*

SEQ ID NO: 3

TACGAGAGTTTGATCCTGGCTCAGGATGAACGCTGGCGGCGTGCCTAACACATGCAAGTCGAGCGAAG
CGCTGTTTTCAGAATCTTCGGAGGAAGAGGACAGTGACTGAGCGGCGGACGGGTGAGTAACGCGTGGG
CAACCTGCCTCATACAGGGGGATAACAGTTAGAAATGACTGCTAATACCGCATAAGCGCACAGGACCG
CATGGTGTAGTGTGAAAAACTCCGGTGGTATGAGATGGACCCGCGTCTGATTAGGTAGTTGGTGGGGT
AAAGGCCTACCAAGCCGACGATCAGTAGCCGACCTGAGAGGGTGACCGGCCACATTGGGACTGAGACA
CGGCCCAAACTCCTACGGGAGGCAGCAGTGGGGAATATTGCACAATGGGGGAAACCCTGATGCAGCGA
CGCCGCGTGAAGGAAGAAGTATTTCGGTATGTAAACTTCTATCAGCAGGGAAGAAAATGACGGTACCT
GAGTAAGAAGCACCGGCTAAATACGTGCCAGCAGCCGCGGTAATACGTATGGTGCAAGCGTTATCCGG
ATTTACTGGGTGTAAAGGGAGCGTAGACGGATAGGCAAGTCTGGAGTGAAAACCCAGGGCTCAACCCT
GGGACTGCTTTGGAAACTGCAGATCTGGAGTGCCGGAGAGGTAAGCGGAATTCCTAGTGTAGCGGTGA
AATGCGTAGATATTAGGAGGAACACCAGTGGCGAAGGCGGCTTACTGGACGGTGACTGACGTTGAGGC
TCGAAAGCGTGGGGAGCAAACAGGATTAGATACCCTGGTAGTCCACGCCGTAAACGATGACTACTAGG
TGTCGGTGTGCAAAGCACATCGGTGCCGCAGCAAACGCAATAAGTAGTCCACCTGGGGAGTACGTTCG
CAAGAATGAAACTCAAAGGAATTGACGGGGACCCGCACAAGCGGTGGAGCATGTGGTTTAATTCGAAG
CAACGCGAAGAACCTTACCTGGTCTTGACATCCGGATGACGGGCGAGTAATGTCGCCGTCCCTTCGGG
GCGTCCGAGACAGGTGGTGCATGGTTGTCGTCAGCTCGTGTCGTGAGATGTTGGGTTAAGTCCCGCAA

```
CGAGCGCAACCCTTATCTTCAGTAGCCAGCATATAAGGTGGGCACTCTGGAGAGACTGCCAGGGAGAA

CCTGGAGGAAGGTGGGGATGACGTCAAATCATCATGCCCCTTATGGCCAGGGCTACACACGTGCTACA

ATGGCGTAAACAAAGGGAAGCGAGAGGGTGACCTGGAGCGAATCCCAAAAATAACGTCTCAGTTCGGA

TTGTAGTCTGCAACTCGACTACATGAAGCTGGAATCGCTAGTAATCGCGGATCAGCATGCCGCGGTGA

ATACGTTCCCGGGTCTTGTACACACCGCCCGTCACACCATGGGAGTCAGTAACGCCCGAAGCCAGTGA

CCCAACCTTAGAGGAGGGAGCTGTCGAAGGCGGGACGGATAACTGGGGTGAAGTCGTAACAAGGTAGC

CGTATCGGAAGGTGCGGCTGGATCACCTCCTTT
```

Strain 4 16S ribosomal RNA *Clostridium symbiosum*

SEQ ID NO: 4

```
ATGAGAGTTTGATCCTGGCTCAGGATGAACGCTGGCGGCGTGCCTAACACATGCAAGTCGAACGAAGC

GATTTAACGGAAGTTTTCGGATGGAAGTTGAATTGACTGAGTGGCGGACGGGTGAGTAACGCGTGGGT

AACCTGCCTTGTACTGGGGGACAACAGTTAGAAATGACTGCTAATACCGCATAAGCGCACAGTATCGC

ATGATACAGTGTGAAAAACTCCGGTGGTACAAGATGGACCCGCGTCTGATTAGCTAGTTGGTAAGGTA

ACGGCTTACCAAGGCGACGATCAGTAGCCGACCTGAGAGGGTGACCGGCCACATTGGGACTGAGACAC

GGCCCAAACTCCTACGGGAGGCAGCAGTGGGGAATATTGCACAATGGGCGAAAGCCTGATGCAGCGAC

GCCGCGTGAGTGAAGAAGTATTTCGGTATGTAAAGCTCTATCAGCAGGGAAGAAAATGACGGTACCTG

ACTAAGAAGCCCCGGCTAACTACGTGCCAGCAGCCGCGGTAATACGTAGGGGGCAAGCGTTATCCGGA

TTTACTGGGTGTAAAGGGAGCGTAGACGGTAAAGCAAGTCTGAAGTGAAAGCCCGCGGCTCAACTGCG

GGACTGCTTTGGAAACTGTTTAACTGGAGTGTCGGAGAGGTAAGTGGAATTCCTAGTGTAGCGGTGAA

ATGCGTAGATATTAGGAGGAACACCAGTGGCGAAGGCGACTTACTGGACGATAACTGACGTTGAGGCT

CGAAAGCGTGGGGAGCAAACAGGATTAGATACCCTGGTAGTCCACGCCGTAAACGATGAATACTAGGT

GTTGGGGAGCAAAGCTCTTCGGTGCCGTCGCAAACGCAGTAAGTATTCCACCTGGGGAGTACGTTCGC

AAGAATGAAACTCAAAGGAATTGACGGGGACCCGCACAAGCGGTGGAGCATGTGGTTTAATTCGAAGC

AACGCGAAGAACCTTACCAGGTCTTGACATCGATCCGACGGGGAGTAACGTCCCCTTCCCTTCGGGG

CGGAGAAGACAGGTGGTGCATGGTTGTCGTCAGCTCGTGTCGTGAGATGTTGGGTTAAGTCCCGCAAC

GAGCGCAACCCTTATTCTAAGTAGCCAGCGGTTCGGCCGGGAACTCTTGGGAGACTGCCAGGGATAAC

CTGGAGGAAGGTGGGGATGACGTCAAATCATCATGCCCCTTATGATCTGGGCTACACACGTGCTACAA

TGGCGTAAACAAAGAGAAGCAAGACCGCGAGGTGGAGCAAATCTCAAAAATAACGTCTCAGTTCGGAC

TGCAGGCTGCAACTCGCCTGCACGAAGCTGGAATCGCTAGTAATCGCGAATCAGAATGTCGCGGTGAA

TACGTTCCCGGGTCTTGTACACACCGCCCGTCACACCATGGGAGTCAGTAACGCCCGAAGTCAGTGAC

CCAACCGCAAGGAGGGAGCTGCCGAAGGCGGGACCGATAACTGGGGTGAAGTCGTAACAAGGTAGCCG

TATCGGAAGGTGCGGCTGGATCACCTCCTTT
```

Strain 5 16S ribosomal RNA *Blautia producta*

SEQ ID NO: 5

```
ATCAGAGAGTTTGATCCTGGCTCAGGATGAACGCTGGCGGCGTGCTTAACACATGCAAGTCGAGCGAA

GCACTTAAGTGGATCTCTTCGGATTGAAGCTTATTTGACTGAGCGGCGGACGGGTGAGTAACGCGTGG

GTAACCTGCCTCATACAGGGGGATAACAGTTAGAAATGGCTGCTAATACCGCATAAGCGCACAGGACC

GCATGGTCTGGTGTGAAAAACTCCGGTGGTATGAGATGGACCCGCGTCTGATTAGCTAGTTGGAGGGG

TAACGGCCCACCAAGGCGACGATCAGTAGCCGGCCTGAGAGGGTGAACGGCCACATTGGGACTGAGAC

ACGGCCCAGACTCCTACGGGAGGCAGCAGTGGGGAATATTGCACAATGGGGGAAACCCTGATGCAGCG

ACGCCGCGTGAAGGAAGAAGTATCTCGGTATGTAAACTTCTATCAGCAGGGAAGAAAATGACGGTACC

TGACTAAGAAGCCCCGGCTAACTACGTGCCAGCAGCCGCGGTAATACGTAGGGGGCAAGCGTTATCCG
```

-continued

```
GATTTACTGGGTGTAAAGGGAGCGTAGACGGAAGAGCAAGTCTGATGTGAAAGGCTGGGCTTAACCC

CAGGACTGCATTGGAAACTGTTTTTCTAGAGTGCCGGAGAGGTAAGCGGAATTCCTAGTGTAGCGGTG

AAATGCGTAGATATTAGGAGGAACACCAGTGGCGAAGGCGGCTTACTGGACGGTAACTGACGTTGAGG

CTCGAAAGCGTGGGGAGCAAACAGGATTAGATACCCTGGTAGTCCACGCCGTAAACGATGAATACTAG

GTGTCGGGTGGCAAAGCCATTCGGTGCCGCAGCAAACGCAATAAGTATTCCACCTGGGGAGTACGTTC

GCAAGAATGAAACTCAAAGGAATTGACGGGGACCCGCACAAGCGGTGGAGCATGTGGTTTAATTCGAA

GCAACGCGAAGAACCTTACCAAGTCTTGACATCCCTCTGACCGGCCCGTAACGGGCCTTCCCTTCGG

GGCAGAGGAGACAGGTGGTGCATGGTTGTCGTCAGCTCGTGTCGTGAGATGTTGGGTTAAGTCCCGCA

ACGAGCGCAACCCCTATCCTTAGTAGCCAGCAGGTGAAGCTGGGCACTCTAGGGAGACTGCCGGGGAT

AACCCGGAGGAAGGCGGGGACGACGTCAAATCATCATGCCCCTTATGATTTGGGCTACACACGTGCTA

CAATGGCGTAAACAAAGGGAAGCGAGACAGCGATGTTGAGCAAATCCCAAAAATAACGTCCCAGTTCG

GACTGCAGTCTGCAACTCGACTGCACGAAGCTGGAATCGCTAGTAATCGCGAATCAGAATGTCGCGGT

GAATACGTTCCCGGGTCTTGTACACACCGCCCGTCACACCATGGGAGTCAGTAACGCCCGAAGTCAGT

GACCCAACCTTACAGGAGGGAGCTGCCGAAGGCGGGACCGATAACTGGGGTGAAGTCGTAACAAGGTA

GCCGTATCGGAAGGTGCGGCTGGATCACCTCCTTT
```

Strain 6 16S ribosomal RNA *Dorea Longicatena*

SEQ ID NO: 6

```
AACGAGAGTTTGATCCTGGCTCAGGATGAACGCTGGCGGCGTGCTTAACACATGCAAGTCGAGCGAAG

CACTTAAGTTTGATTCTTCGGATGAAGACTTTTGTGACTGAGCGGCGGACGGGTGAGTAACGCGTGGG

TAACCTGCCTCATACAGGGGGATAACAGTTAGAAATGACTGCTAATACCGCATAAGACCACGGTACCG

CATGGTACAGTGGTAAAAACTCCGGTGGTATGAGATGGACCCGCGTCTGATTAGGTAGTTGGTGGGGT

AACGGCCTACCAAGCCGACGATCAGTAGCCGACCTGAGAGGGTGACCGGCCACATTGGGACTGAGACA

CGGCCCAGACTCCTACGGGAGGCAGCAGTGGGGAATATTGCACAATGGAGGAAACTCTGATGCAGCGA

CGCCGCGTGAAGGATGAAGTATTTCGGTATGTAAACTTCTATCAGCAGGGAAGAAAATGACGGTACCT

GACTAAGAAGCCCCGGCTAACTACGTGCCAGCAGCCGCGGTAATACGTAGGGGGCAAGCGTTATCCGG

ATTTACTGGGTGTAAAGGGAGCGTAGACGGCACGGCAAGCCAGATGTGAAAGCCCGGGGCTCAACCCC

GGGACTGCATTTGGAACTGCTGAGCTAGAGTGTCGGAGAGGCAAGTGGAATTCCTAGTGTAGCGGTGA

AATGCGTAGATATTAGGAGGAACACCAGTGGCGAAGGCGGCTTGCTGGACGATGACTGACGTTGAGGC

TCGAAAGCGTGGGGAGCAAACAGGATTAGATACCCTGGTAGTCCACGCCGTAAACGATGACTGCTAGG

TGTCGGGTGGCAAAGCCATTCGGTGCCGCAGCTAACGCAATAAGCAGTCCACCTGGGGAGTACGTTCG

CAAGAATGAAACTCAAAGGAATTGACGGGACCCGCACAAGCGGTGGAGCATGTGGTTTAATTCGAAG

CAACGCGAAGAACCTTACCTGATCTTGACATCCCGATGACCGCTTCGTAATGGAAGCTTTTCTTCGGA

ACATCGGTGACAGGTGGTGCATGGTTGTCGTCAGCTCGTGTCGTGAGATGTTGGGTTAAGTCCCGCAA

CGAGCGCAACCCCTATCTTCAGTAGCCAGCAGGTTAAGCTGGGCACTCTGGAGACTGCCAGGGATA

ACCTGGAGGAAGGTGGGGATGACGTCAAATCATCATGCCCCTTATGACCAGGGCTACACACGTGCTAC

AATGGCGTAAACAAAGAGAAGCGAACTCGCGAGGGTAAGCAAATCTCAAAAATAACGTCTCAGTTCGG

ATTGTAGTCTGCAACTCGACTACATGAAGCTGGAATCGCTAGTAATCGCAGATCAGAATGCTGCGGTG

AATACGTTCCCGGGTCTTGTACACACCGCCCGTCACACCATGGGAGTCAGTAACGCCCGAAGTCAGTG

ACCCAACCGTAAGGAGGGAGCTGCCGAAGGTGGGACCGATAACTGGGGTGAAGTCGTAACAAGGTAGC

CGTATCGGAAGGTGCGGCTGGATCACCTCCTTT
```

-continued

Strain 7 16S ribosomal RNA *Erysipelotrichaceae bacterium*

SEQ ID NO: 7

ATGGAGAGTTTGATCCTGGCTCAGGATGAACGCTGGCGGCATGCCTAATACATGCAAGTCGAACGAAG

TTTCGAGGAAGCTTGCTTCCAAAGAGACTTAGTGGCGAACGGGTGAGTAACACGTAGGTAACCTGCCC

ATGTGTCCGGGATAACTGCTGGAAACGGTAGCTAAAACCGGATAGGTATACAGAGCGCATGCTCAGTA

TATTAAAGCGCCCATCAAGGCGTGAACATGGATGGACCTGCGGCGCATTAGCTAGTTGGTGAGGTAAC

GGCCCACCAAGGCGATGATGCGTAGCCGGCCTGAGAGGGTAAACGGCCACATTGGGACTGAGACACGG

CCCAAACTCCTACGGGAGGCAGCAGTAGGGAATTTTCGTCAATGGGGGAAACCCTGAACGAGCAATGC

CGCGTGAGTGAAGAAGGTCTTCGGATCGTAAAGCTCTGTTGTAAGTGAAGAACGGCTCATAGAGGAAA

TGCTATGGGAGTGACGGTAGCTTACCAGAAAGCCACGGCTAACTACGTGCCAGCAGCCGCGGTAATAC

GTAGGTGGCAAGCGTTATCCGGAATCATTGGGCGTAAAGGGTGCGTAGGTGGCGTACTAAGTCTGTAG

TAAAAGGCAATGGCTCAACCATTGTAAGCTATGGAAACTGGTATGCTGGAGTGCAGAAGAGGGCGATG

GAATTCCATGTGTAGCGGTAAAATGCGTAGATATATGGAGGAACACCAGTGGCGAAGGCGGTCGCCTG

GTCTGTAACTGACACTGAGGCACGAAAGCGTGGGGAGCAAATAGGATTAGATACCCTAGTAGTCCACG

CCGTAAACGATGAGAACTAAGTGTTGGAGGAATTCAGTGCTGCAGTTAACGCAATAAGTTCTCCGCCT

GGGGAGTATGCACGCAAGTGTGAAACTCAAAGGAATTGACGGGGCCCGCACAAGCGGTGGAGTATGT

GGTTTAATTCGAAGCAACGCGAAGAACCTTACCAGGCCTTGACATGGAAACAAATACCCTAGAGATAG

GGGGATAATTATGGATCACACAGGTGGTGCATGGTTGTCGTCAGCTCGTGTCGTGAGATGTTGGGTTA

AGTCCCGCAACGAGCGCAACCCTTGTCGCATGTTACCAGCATCAAGTTGGGGACTCATGCGAGACTGC

CGGTGACAAACCGGAGGAAGGTGGGGATGACGTCAAATCATCATGCCCCTTATGGCCTGGGCTACACA

CGTACTACAATGGCGGCCACAAAGAGCAGCGACACAGTGATGTGAAGCGAATCTCATAAAGGTCGTCT

CAGTTCGGATTGAAGTCTGCAACTCGACTTCATGAAGTCGGAATCGCTAGTAATCGCAGATCAGCATG

CTGCGGTGAATACGTTCTCGGGCCTTGTACACACCGCCCGTCAAACCATGGGAGTCAGTAATACCCGA

AGCCGGTGGCATAACCGTAAGGAGTGAGCCGTCGAAGGTAGGACCGATGACTGGGGTTAAGTCGTAAC

AAGGTATCCCTACGGGAACGTGGGGATGGATCACCTCCTTT

Strain 8 16S ribosomal RNA *Subdoligranulum spp*

SEQ ID NO: 8

TATTGAGAGTTTGATCCTGGCTCAGGATGAACGCTGGCGGCGTGCTTAACACATGCAAGTCGAACGGG

GTGCTCATGACGGAGGATTCGTCCAACGGATTGAGTTACCTAGTGGCGGACGGGTGAGTAACGCGTGA

GGAACCTGCCTTGGAGAGGGGAATAACACTCCGAAAGGAGTGCTAATACCGCATGATGCAGTTGGGTC

GCATGGCTCTGACTGCCAAAGATTTATCGCTCTGAGATGGCCTCGCGTCTGATTAGCTAGTAGGCGGG

GTAACGGCCCACCTAGGCGACGATCAGTAGCCGGACTGAGAGGTTGACCGGCCACATTGGGACTGAGA

CACGGCCCAGACTCCTACGGGAGGCAGCAGTGGGGAATATTGGGCAATGGGCGCAAGCCTGACCCAGC

AACGCCGCGTGAAGGAAGAAGGCTTTCGGGTTGTAAACTTCTTTTGTCGGGGACGAAACAAATGACGG

TACCCGACGAATAAGCCACGGCTAACTACGTGCCAGCAGCCGCGGTAATACGTAGGTGGCAAGCGTTA

TCCGGATTTACTGGGTGTAAAGGGCGTGTAGGCGGGATTGCAAGTCAGATGTGAAAACTGGGGGCTCA

ACCTCCAGCCTGCATTTGAAACTGTAGTTCTTGAGTGCTGGAGAGGCAATCGGAATTCCGTGTGTAGC

GGTGAAATGCGTAGATATACGGAGGAACACCAGTGGCGAAGGCGGATTGCTGGACAGTAACTGACGCT

GAGGCGCGAAAGCGTGGGGAGCAAACAGGATTAGATACCCTGGTAGTCCACGCCGTAAACGATGGATA

CTAGGTGTGGGGGGTCTGACCCCCTCCGTGCCGCAGTTAACACAATAAGTATCCCACCTGGGGAGTAC

GATCGCAAGGTTGAAACTCAAAGGAATTGACGGGGGCCCGCACAAGCGGTGGAGTATGTGGTTTAATT

CGAAGCAACGCGAAGAACCTTACCAGGGCTTGACATCCCACTAACGAAGCAGAGATGCATTAGGTGCC

CTTCGGGGAAAGTGGAGACAGGTGGTGCATGGTTGTCGTCAGCTCGTGTCGTGAGATGTTGGGTTAAG

-continued

```
TCCCGCAACGAGCGCAACCCTTATTGTTAGTTGCTACGCAAGAGCACTCTAGCGAGACTGCCGTTGAC

AAAACGGAGGAAGGTGGGGACGACGTCAAATCATCATGCCCCTTATGTCCTGGGCCACACACGTACTA

CAATGGTGGTTAACAGAGGGAGGCAATACCGCGAGGTGGAGCAAATCCCTAAAAGCCATCCCAGTTCG

GATTGCAGGCTGAAACCCGCCTGTATGAAGTTGGAATCGCTAGTAATCGCGGATCAGCATGCCGCGGT

GAATACGTTCCCGGGCCTTGTACACACCGCCCGTCACACCATGAGAGTCGGGAACACCCGAAGTCCGT

AGCCTAACCGCAAGGAGGGCGCGGCCGAAGGTGGGTTCGATAATTGGGGTGAAGTCGTAACAAGGTAG

CCGTATCGGAAGGTGCGGCTGGATCACCTCCTTT
```

This invention is not limited in its application to the details of construction and the arrangement of components set forth in the following description or illustrated in the drawings. The invention is capable of other embodiments and of being practiced or of being carried out in various ways. Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

Unless otherwise defined herein, scientific and technical terms used in connection with the present disclosure shall have the meanings that are commonly understood by those of ordinary skill in the art. Further, unless otherwise required by context, singular terms shall include pluralities and plural terms hall include the singular. The methods and techniques of the present disclosure are generally performed according to conventional methods well-known in the art. Generally, nomenclatures used in connection with, and techniques of biochemistry, enzymology, molecular and cellular biology, microbiology, virology, cell or tissue culture, genetics and protein and nucleic chemistry described herein are those well-known and commonly used in the art. The methods and techniques of the present disclosure are generally performed according to conventional methods well known in the art and as described in various general and more specific references that are cited and discussed throughout the present specification unless otherwise indicated.

The present invention is further illustrated by the following Examples, which in no way should be construed as further limiting. The entire contents of all of the references (including literature references, issued patents, published patent applications, and co-pending patent applications) cited throughout this application are hereby expressly incorporated by reference, in particular for the teaching that is referenced hereinabove. However, the citation of any reference is not intended to be an admission that the reference is prior art.

EXAMPLES

Example 1

Overview

A variety of lyophilization formulations were assessed for the lyophilization of the anaerobic bacterium *Dorea longicatena*. The experimental design is depicted in FIG. 1.

Bacterial Culture

An inoculum of *Dorea longicatena* was started from a single colony until it reached an OD600 of about 0.68, corresponding to late log phase, and then transferred to a larger flask. Aliquots of 40 mls of bacteria were pelleted. The pelleted bacteria were at $1.6 \times 10^7$ cfu/ml. (cfu=colony forming units)

Lyophilization Buffer Preparation

The formulations depicted in FIG. 2 and Table 2 were prepared in an anaerobic chamber. The mannitol and sorbitol were crystalline, while the sucrose and trehalose were amorphous. In addition to the formulation components shown in FIG. 2, all formulations included 1% yeast extract, and 0.05% cysteine. The concentrations of the histidine and tris-base buffer was 20 mM. Formulations were filtered through a 0.22 microM filter. Sixteen 50 ml conical tubes contain the bacterial pellets were stored in a chamber at 2-8° C. were provided The number of bacteria in each tube was $1.6 \times 10^7$ cfu/ml. Pellets were washed with 20 ml lyophilization formulation twice and spun at 3900 rpm for 10 minutes. The osmolality of the formulations ranged from 292 to 329 mosmole. The washed pellets were re-suspended with 25 ml lyophilization buffer and 5 vials were prepared for each lyophilization formulation. Four vials were used in the lyophilization cycle and one vial was kept at −80° C. as a control. The vials were partially stoppered with 20-mm diameter Type I elastomeric chlorobutyl stoppers. One of the sixteen 50 ml conical tubes was washed with culture media and used as a control for the lyophilization cycle.

Bacterial pellets used as controls were washed with 12 ml cell culture medium twice, and spun at 3900 rpm for 10 minutes. The cells were subsequently re-suspended with 25 ml cell culture medium and a total of 5 vials were filled: 5 ml fill in a 20 ml vial. Four vials were lyophilized and one was kept at −80° C. as a control. The vials were partially stoppered with 20 mm diameter Type I elastomeric chlorobutyl stoppers.

TABLE 2

Formulations used in Example 1.

| Formulation # | Buffer/pH | Mannitol | Trehalose | Sorbitol | Sucrose | Lactose | Osmolality |
|---|---|---|---|---|---|---|---|
| 1 | His/6.5 | 4% | | | | | 318 |
| 2 | His/7.0 | 4% | | | | | 314 |
| 3 | Tris/7.0 | 4% | | | | | 307 |
| 4 | Tris/7.5 | 4% | | | | | 300 |

TABLE 2-continued

Formulations used in Example 1.

| Formulation # | Buffer/pH | Mannitol | Trehalose | Sorbitol | Sucrose | Lactose | Osmolality |
|---|---|---|---|---|---|---|---|
| 5 | His/6.5 | | 8% | | | | 304 |
| 6 | His/7.0 | | 8% | | | | 302 |
| 7 | Tris/7.0 | | 8% | | | | 312 |
| 8 | Tris/7.5 | | 8% | | | | 318 |
| 9 | His/6.5 | | | | 8% | | 316 |
| 10 | His/7.0 | | | | 8% | | 317 |
| 11 | Tris/7.0 | | | | 8% | | 308 |
| 12 | His/7.0 | | | | 8% | | 309 |
| 13 | His/7.0 | | | 4% | | | 304 |
| 14 | Tris/7.0 | | | 4% | | | 292 |
| 15 | His/7.0 | 4% | | | | 4% | 329 |
| 16 | Culture Media | | | | | | |

Lyophilization Cycle:

The lyophilization cycle was performed with the lyophilization parameters shown in Table 3 below.

TABLE 3

Lyophilization cycle

| Step | Temperature | Temperature Ramp (° C./min) | Hold in hrs | Pressure |
|---|---|---|---|---|
| Loading | 4° C. | 1° C./min | 2 | N/A |
| Freeze | −50° C. | 1° C./min. | 2 | N/A |
| Primary Drying | −25° C. | 1° C./min | 67 | 100 mTorr |
| Secondary Drying | +20° C. | 1° C./min | 20.9 | 100 mTorr |

Upon completion of the lyophilization cycle, back fill of nitrogen was performed to reach 600,000 mTorr and then vials were stoppered to keep $N_2$ in the vials in vacuum. Once the vials were stoppered, the back fill was completed to reach 760,000 mtorr. The lyophilized products in glass vials were retrieved from the lyophilizer and promptly sealed with the aluminum crimp-caps to prevent the atmospheric air contamination and to prevent the $N_2$ releasing from the vial. The completion of primary and secondary drying stages was determined based on the Pirani pressure. All lyophilized containers were stored at −20° C. for storage prior to viability testing.

The samples were cooled to 4° C. for 2 hrs and frozen at −50° C. for 2 hrs. As the 16 formulation will have different Tg', the primary drying was set to −25° C. It is known the amorphous sugars such as sucrose have a transition of −32° C. and the crystalline mannitol has the eutectic temperature of about 15° C. The primary drying at −25° C. was selected so that the majority of the formulations would stay below transition or eutectic temperature during lyophilization. The pressure profile suggests that Pirani pressure reached 100 mtorr at about 63 hrs of lyophilization. The primary drying was extended to 73 hrs to ensure the ending of primary drying. The bound water was removed during the secondary drying. Based on the Pirani pressure profile, the secondary drying was completed at 81 hrs of lyophilization. The lyophilization was extended to 88 hrs to ensure the complete removal of the bound water.

Results of Lyophilization Cycle

Figure 3:
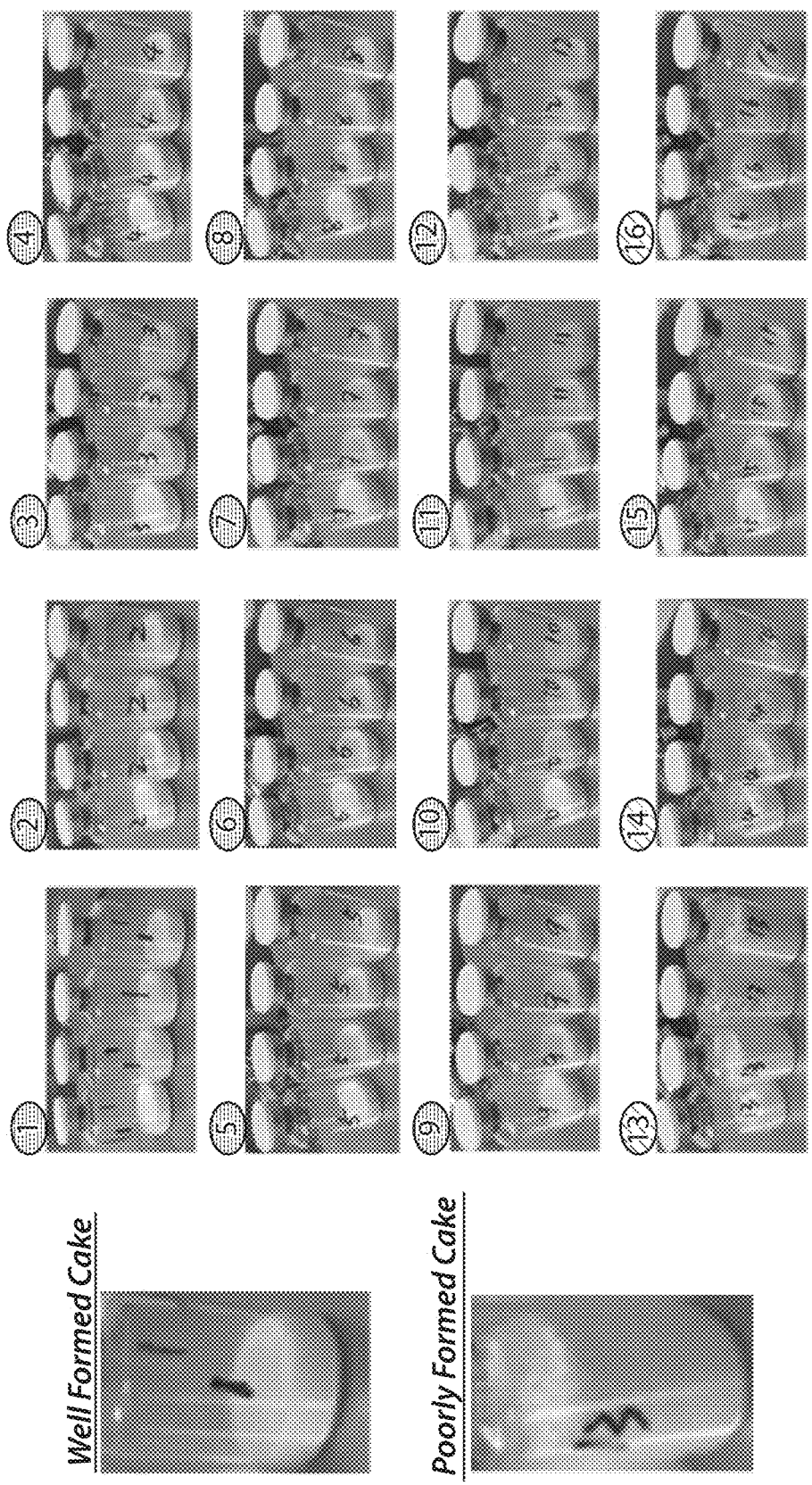
FIG. 3 shows photographs of representative lyophilization cakes generated in Example 1.

The physical appearance of the lyophilized formulations are shown in FIG. 3. The data indicates that except the formulation containing the crystalline sorbitol and formulation containing culture media, all the cakes of other 13 formulations are not collapsed and are intact. The cake of the formulation containing sorbitol were collapsed and raised with the bubbling. Similarly, the formulation containing culture media alone also collapsed.

Based on the cake appearances, this lyophilization run looks acceptable for the formulation containing amorphous trehalose and sucrose and crystalline mannitol. The cakes of the formulation containing sorbitol and culture media collapsed after lyophilization.

Viability of Lyophilized Samples.

The lyophilized cakes were moved into the anaerobic chamber, opened and resuspended in 5 ml of culture media as the cakes were representative of a 5 ml sample. (resuspended in culture media HiVeg media). Dilutions were prepared from $10^1$ to $10^6$ to $10^7$ and 100 microliter of the each dilution was dispensed on an Eggerth Gagnon plate and spread with help of sterile glass beads. Plating was done on pre-reduced Eggerth Gagnon plates enriched with 5% horse blood. Incubation was done at 37° C. in the incubator in the anaerobic chamber. Colony forming units were counted 48-72 hours after plating.

The combined results of the lyophilization experiment and the viability of the assessed samples is shown in FIG. 4 and Table 4. The best results are obtained with His pH 7.0 or Tris pH 7.5 as the buffer and sucrose or trehalose as the sugar.

TABLE 4

Results of formulation experiment

| Formulation # | Buffer/pH | Mannitol | Trehalose | Sorbitol | Sucrose | Lactose | Viability (CFU) |
|---|---|---|---|---|---|---|---|
| 1 | His/6.5 | 4% | | | | | 0 |
| 2 | His/7.0 | 4% | | | | | 0 |
| 3 | Tris/7.0 | 4% | | | | | 0 |
| 4 | Tris/7.5 | 4% | | | | | 0 |
| 5 | His/6.5 | | 8% | | | | $2.8 \times 10^3$ |

TABLE 4-continued

Results of formulation experiment

| Formulation # | Buffer/pH | Mannitol | Trehalose | Sorbitol | Sucrose | Lactose | Viability (CFU) |
|---|---|---|---|---|---|---|---|
| 6 | His/7.0 | | 8% | | | | $9.5 \times 10^4$ |
| 7 | Tris/7.0 | | 8% | | | | $1.0 \times 10^4$ |
| 8 | Tris/7.5 | | 8% | | | | $1.7 \times 10^5$ |
| 9 | His/6.5 | | | | 8% | | ~150 |
| 10 | His/7.0 | | | | 8% | | $3.1 \times 10^5$ |
| 11 | Tris/7.0 | | | | 8% | | $2.9 \times 10^4$ |
| 12 | Tris/7.5 | | | | 8% | | $2.3 \times 10^5$ |
| 13 | His/7.0 | | | 4% | | | $6.4 \times 10^4$ |
| 14 | Tris/7.0 | | | 4% | | | $2.3 \times 10^5$ |
| 15 | His/7.0 | 4% | | | | 4% | 0 |
| 16 | Media | | | | | | ~350 |

Example 2

Overview

This study assessed lyophilization formulations and components for the lyophilization of the anaerobic bacterium *Dorea longicatena*.

Bacterial Culture

An inoculum of *Dorea longicatena* was started from a single colony in 50 mL centrifuge tubes containing 40 mL of Vegitone media. The inoculum was allowed to grow overnight and two tubes were used to inoculate 750 mL of Vegitone in a 1 Liter bottle at a starting OD of 0.025. This was allowed to grow for twenty hours and was harvested at an OD of 0.68. Aliquots of 40 mL were added to sixteen 50 mL centrifuge tubes. The tubes were spun down at 3560 RCF for 10 minutes and the supernatants were discarded. The tubes were sealed and placed in an BD EZPak Anaerobic Container with a BD EZPak Gas Generating Pouch (Becton, Dicksinon and Company; Franklin Lakes, N.Y.) to ensure an anaerobic environment. The box was placed in a 2-8° C. refrigerator prior to viability testing.

Lyophilization Buffer Preparation and Lyophilization Cycle

The formulations presented in Table 5 were prepared to assess lyophilization of the bacterial cultures. Each formulation tested had 1% yeast extract and 0.05% L-Cysteine added. Yeast extract was added to provide each strain animal-free nutrients. L-Cysteine was added as a reducing agent to mitigate oxygen exposure.

Prior to viability testing, the vials were resuspended in 25 mL of media and plated to determine starting viabilities.

Each sample was washed twice using the formulation buffers shown in Table 5. A volume of 25 mL was used for the final resuspension, to concentrate the starting sample. Each formulation shown in Table 5 had aliquots of 5 mL added to separate 20 mL vials and were then lyophilized using a primary drying of −25° C. at 100 mTorr and using a secondary drying of 20° C. at 100 mTorr.

Viability of Lyophilized Samples

After lyophilization, the final viable cell counts were determined by resuspending each vial in 5 mL of media and plating on EGHB (Table 6). The data indicates that bacteria that were lyophilized in formulations containing sucrose or trehalose as a lyoprotectant were able to be recovered. Formulations with mannitol results in no recoverable, viable bacteria, and using culture media only for lyophilization resulted in poor recovery. Formulations with sorbitol had poor lyophilization cake formation. Histidine was selected as the buffer, as it resulted in viability with both sucrose and trehalose. Formulations 6 and 10 were further evaluated.

TABLE 5

Lyophilization Formulations

| Formulation | 20 mM Histidine (pH) | 20 mM Tris (pH) | Mannitol (%) | Trehalose (%) | Sorbitol (%) | Sucrose (%) | Lactose (%) | Culture Medium (mL) | mOsmo/kg |
|---|---|---|---|---|---|---|---|---|---|
| 1 | 6.5 | | 4 | | | | | | 318 |
| 2 | 7 | | 4 | | | | | | 314 |
| 3 | | 7 | 4 | | | | | | 307 |
| 4 | | 7.5 | 4 | | | | | | 300 |
| 5 | 6.5 | | | 7.5 | | | | | 304 |
| 6 | 7 | | | 7.5 | | | | | 302 |
| 7 | | 7 | | 7.5 | | | | | 312 |
| 8 | | 7.5 | | 7.5 | | | | | 318 |
| 9 | 6.5 | | | | | 7 | | | 316 |
| 10 | 7 | | | | | 7 | | | 317 |
| 11 | | 7 | | | | 7 | | | 308 |
| 12 | 7 | | | | | 7 | | | 309 |
| 13 | 7 | | | | 4 | | | | 304 |
| 14 | | 7 | | | 4 | | | | 292 |
| 15 | 7 | | 4 | | | | 4 | | 329 |
| 16 | | | | | | | | 25 | N/A |

TABLE 6

Viability of lyophilized samples

| Formulation* | Formulation | Count A | Count B | Average | SD |
|---|---|---|---|---|---|
| 1 | 4% mannitol-His pH 6.5 | 0 | 0 | 0 | 0 |
| 2 | 4% mannitol-His pH 7.0 | N/A^ | 0 | 0 | |
| 3 | 4% mannitol-Tris-pH 7.0 | 0 | 0 | 0 | 0 |
| 4 | 4% mannitol-Tris-pH 7.5 | 0 | 0 | 0 | 0 |
| 5 | 7.5% Trehalose His pH 6.5 | $3.30 \times 10^3$ | $2.30 \times 10^3$ | $2.80 \times 10^3$ | $7.07 \times 10^2$ |
| 6 | 7.5% Trehalose His pH 7.0 | $8.00 \times 10^4$ | $1.10 \times 10^5$ | $9.50 \times 10^4$ | $2.12 \times 10^4$ |
| 7 | 7.5% Trehalose Tris-pH 7.0 | $1.00 \times 10^3$ | $1.90 \times 10^4$ | $1.00 \times 10^4$ | $1.27 \times 10^4$ |
| 8 | 7.5% Trehalose Tris-pH 7.5 | $5.20 \times 10^4$ | $2.80 \times 10^5$ | $1.66 \times 10^5$ | $1.61 \times 10^5$ |
| 9 | 7% Sucrose-His pH 6.5 | $3.00 \times 10^2$ | 0 | 150 | 212 |
| 10 | 7% Sucrose-His pH 7.0 | $1.50 \times 10^4$ | $6.00 \times 10^5$ | $3.08 \times 10^5$ | $4.14 \times 10^5$ |
| 11 | 7% Sucrose-Tris-pH 7.0 | $5.70 \times 10^4$ | 0 | $2.85 \times 10^4$ | $4.03 \times 10^4$ |
| 12 | 7% Sucrose-Tris-pH 7.5 | $1.90 \times 10^5$ | $2.60 \times 10^5$ | $2.25 \times 10^5$ | $4.95 \times 10^4$ |
| 13 | 4% sorbitol His-pH 7.0 | $8.40 \times 10^4$ | $4.30 \times 10^4$ | $6.35 \times 10^4$ | $2.90 \times 10^4$ |
| 14 | 4% sorbitol Tris-pH 7.0 | $1.20 \times 10^5$ | $3.40 \times 10^5$ | $2.30 \times 10^5$ | $1.56 \times 10^5$ |
| 15 | 4% mannitol + 4% Lactose-His pH 7.0 | 0 | 0 | 0 | 0 |
| 16 | Culture Medium | 100 | 600 | 350 | 353 |

*Formulations correspond to the formulations presented in Table 5.
^sample contaminated; no value determinable.

Example 3

Overview

A selected number of optimized lyophilization formulations were assessed for the lyophilization of eight different anaerobic strains. The experimental design is depicted in FIG. 1.

Bacterial Cultures

An inoculum of each of the bacterial strains shown in Table 7 was started from a single colony until it reached the OD shown in Table 8 and then transferred to a larger flask. Aliquots 40 mls of bacteria were pelleted. The cfus of the pelleted bacteria are shown in FIG. 5.

TABLE 7

Bacterial strains used in Example 3

| Strain number | Closest known relative |
|---|---|
| 1 | Clostridium bolteae |
| 2 | Anaerotruncus colihominis |
| 3 | Ruminococcus torques |
| 4 | Clostridium symbiosum |
| 5 | Blautia producta |
| 6 | Dorea longicatena |
| 7 | Erysipelotrichaceae bacterium |
| 8 | Subdoligranulum spp |

Bacterial strains were identified by the closest known relative as identified by sequence homology/identity.

TABLE 8

OD600 of bacterial strains used for Example 3

| Strain | OD (600 nm) |
|---|---|
| 1 | 2.73 |
| 2 | 0.55 |
| 3 | 0.84 |
| 4 | 1.93 |
| 5 | 0.95 |
| 6 | 0.61 |
| 7 | 1.79 |
| 8 | 0.272 |

Lyophilization Buffer Preparation

Two lyophilization formulations were assessed:

Formulation A: 20 mM Histidine pH 7.0, 1% yeast extract, 0.05% cysteine and 7.5% trehalose with osmolality of 305 mOsmo/kg Formulation B: 20 mM Histidine pH 7.0, 1% yeast extract, 0.05% cysteine and 7.0% sucrose with osmolality of 315 mOsmo/kg.

The formulations were prepared in the anaerobic chamber. Sixteen 50 ml conical tubes containing the bacterial pellets were used. The number of bacteria in each tube varied per strain and varied between $1.4 \times 10^7$ and $2.75 \times 10^9$ cfus/ml (See FIG. 5). The bacterial pellets were washed with 20 ml lyophilization formulation twice, and spun at 3900 rpm for 10 minutes. The osmolality of the formulations ranged from 305-315 mosmole. The pellets were re-suspended with 20 ml lyophilization formulation buffer and 4 vials were filled for each (5 ml fill in a 20 ml). Three vials were lyophilized and one vial was kept at −80° C. as a control. The vials were partially stoppered with 20-mm diameter Type I elastomeric chlorobutyl stoppers.

Lyophilization Cycle:

The lyophilization run was performed with the lyophilization parameters shown in Table 9 below.

TABLE 9

Lyophilization cycle

| Step | Temperature | Temperature Ramp (° C./min) | Hold in hrs | Pressure |
|---|---|---|---|---|
| Loading | 4° C. | 1° C./min | 0.1 | NA |
| Freeze | −50° C. | 1° C./min. | 2 | NA |
| Primary Drying | −25° C. | 1° C./min | 66 | 100 mTorr |
| Secondary Drying | +20° C. | 1° C./min | 9.0 | 100 mTorr |

Upon completion of the lyophilization cycle, back fill of nitrogen was performed to reach 600,000 mTorr and then vials were stoppered to keep $N_2$ in the vials in vacuum. Once the vials were stoppered, the back fill was completed to reach 760,000 mtorr. The lyophilized samples in glass vials were retrieved from the lyophilizer and promptly sealed with the aluminum crimp-caps to prevent the atmospheric air contamination and to prevent the $N_2$ releasing from the vial. The completion of primary and secondary drying stages was determined based on the Pirani pressure reaching the set shelf pressure. All lyophilized containers were stored at −20 C prior to viability testing.

The samples were cooled to 4° C. for 10 minutes and frozen at −50° C. for 2 hrs. As the 2 formulation will have different Tg', the primary drying was set to −25° C. It is known that the amorphous sugars such as sucrose have a transition of −32° C. while the Trehalose transition temperature (−29° C.) is about 3° C. higher than sucrose. The primary drying at −25° C. was selected so that the majority of the formulations will stay below transition during lyophilization. The pressure profile suggests that Pirani pressure reached 100 mtorr at about 56 hrs of lyophilization. The primary drying was extended to 66 hrs to ensure the ending of primary drying. The bound water was removed during the secondary drying. Based on the Pirani pressure profile, the secondary drying was completed at 76 hrs of lyophilization.
Results of Lyophilization Cycle The physical appearance of each lyophilized formulation data showed that none of the cakes are collapsed. The color of the lyophilization cakes varied slightly between bacterial strains.
Viability of Lyophilized Samples.

The lyophilized caked were moved into the anaerobic chamber, opened and resuspended in 5 ml of culture media as the cakes were representative of a 5 ml sample.

(Resuspended in peptone yeast extract glucose media with tween). Dilutions were prepped from $10^1$ to $10^6$ to $10^7$ and 100 microliter of the each dilution was dispensed on an Eggerth Gagnon plate and spread with help of sterile glass beads. Plating was done on pre-reduced Eggerth Gagnon plates enriched with 5% horse blood. Incubation was done at 37 degrees in the incubator in the anaerobic chamber. Colony forming units were counted 48-72 hours after plating.

The results of the lyophilization experiment and the viability of the assessed samples is shown in FIG. 5 and Table 10. Formulations A and B provide a good recovery for bacterial strains 2-5 and 7-8.
Assessment of Lyophilization (Freeze-Dry) Versus Freeze Only)

The impact of the lyophilization cycle on bacterial strains in Formulations A and B was assessed by comparing the lyophilization of samples versus freezing the samples only (i.e., freezing the samples at −80° C., but not exposing the samples to a vacuum "freeze-thaw"). Viability of the freeze-thaw samples was assessed in the same way as the viability for the sample that went through the lyophilization cycle.

The results of the freeze-thaw cycle experiment are shown in FIG. 5 and Table 10. Formulations A and B provide a good stability for bacterial strains 2-5 and 7-8. Strains 1 and 6 were further evaluated.

Example 4

Lyophilization formulations for bacterial strains 1 and 6 (*Clostridium bolteae* and *Dorea longicatena*) were further evaluated using additional excipients (Tables 11 and 12) to improve the yield post lyophilization. Strains 1 and 6 were harvested at an OD of 2.83 and 1.27, respectively. The cultures were aliquoted into centrifuge tubes and pelleted at 3560RCF for 10 minutes. The supernatants were discarded and the pellets were placed in an BD EZPak Anaerobic Container with a BD EZPak Gas Generating Pouch until use in the studies.

Prior to viability testing, the pellets were washed twice using the formulation buffers to be tested, aliquoted out 5 mL from the final resuspension into vials and lyophilized them. The lyophilization used a primary drying of −25° C. at 100 mTorr and used a secondary drying of 20° C. at 100 mTorr. The temperature ramp rate used in the lyophilization cycle was increased to 2.5° C./min between conditions, as compared to the 1.0° C./min used in Examples 1-3.

To assess viability of the bacterial strains, the final lyophilized bacteria were resuspended in 5 mL of media and plated to determine the viable cell count after lyophilization. The excipients in the formulations and the results for strain 1 and 6 are shown in Tables 11 and 12, respectively. The initial viable cell counts prior to lyophilization for strain 1 and 6 were of $2.14 \times 10^9$ CFU/mL and $5.15 \times 10^7$ CFU/mL, respectively. The post-lyophilization average is the average of results from two vials.

TABLE 11

Lyophilization Formulation Excipients and Viability of Strain 1

| Condition Formulation # | Additional Excipients | Post Lyo Average | Viability Average |
|---|---|---|---|
| 1 | None | $4.40 \times 10^8$ | 20.59% |
| 2 | 0.05% sodium meta bisulfite | $5.30 \times 10^8$ | 24.80% |
| 3 | 0.05% Ascorbic acid | $4.40 \times 10^8$ | 20.59% |
| 4 | 0.05% Citric acid | $7.60 \times 10^8$ | 35.57% |
| 5 | 0.5% sodium glutamate | $3.75 \times 10^8$ | 17.55% |
| 6 | 0.5% Arginine | $5.75 \times 10^8$ | 26.91% |
| 7 | 5% poloxamer 188 | $8.50 \times 10^5$ | 0.04% |
| 8 | 5% Kollidon 30 | $3.40 \times 10^6$ | 0.16% |
| 9 | Poloxamer + Kollidon 30 | $1.03 \times 10^7$ | 0.48% |

TABLE 10

Viability Results of Example 3

| Bacterial Strain | Initial CFU | Post Lyo CFU (Condition A) | Post Freeze Thaw (Condition A) | Post Lyo CFU (Condition B) | Post Freeze Thaw (Condition B) |
|---|---|---|---|---|---|
| 01 | $1.04 \times 10^8$ | $5 \times 10^7$ | $3 \times 10^7$ | $2 \times 10^6$ | $8 \times 10^7$ |
| 02 | $2.16 \times 10^8$ | $1 \times 10^8$ | $7 \times 10^9$ | $1.5 \times 10^8$ | $1.4 \times 10^{10}$ |
| 03 | $8.1 \times 10^8$ | $8 \times 10^9$ | $3.1 \times 10^{10}$ | $7.5 \times 10^9$ | $1 \times 10^{10}$ |
| 04 | $9.6 \times 10^8$ | $3 \times 10^8$ | $3.2 \times 10^9$ | $3.05 \times 10^9$ | $1.2 \times 10^9$ |
| 05 | $6.7 \times 10^7$ | $1.2 \times 10^9$ | $2.5 \times 10^{10}$ | $1 \times 10^9$ | $2 \times 10^{10}$ |
| 06 | $1.4 \times 10^7$ | $4.4 \times 10^5$ | N/A | $1 \times 10^6$ | $8 \times 10^5$ |
| 07 | $2.75 \times 10^9$ | $4 \times 10^9$ | $5 \times 10^9$ | $4 \times 10^{10}$ | Lawn on $10^7$ |
| 08 | $1.65 \times 10^8$ | $3.1 \times 10^8$ | $3.1 \times 10^9$ | $4.1 \times 10^8$ | $2.4 \times 10^{10}$ |

TABLE 12

Lyophilization Formulation Excipients and Viability of Strain 6

| Condition Formulation # | Additional Excipients | Post-Lyo Average | Viability Average |
|---|---|---|---|
| 1 | None | $6.23 \times 10^6$ | 11.96% |
| 2* | 0.05% sodium meta bisulfite | $4.32 \times 10^7$ | 84.22% |
| 3 | 0.05% Ascorbic acid | $3.56 \times 10^6$ | 6.92% |
| 4* | 0.05% Citric acid | $1.31 \times 10^7$ | 25.35% |
| 5* | 0.5% sodium glutamate | $1.89 \times 10^7$ | 36.72% |
| 6 | 0.5% Arginine | $9.25 \times 10^6$ | 17.97% |
| 7 | 5% poloxamer 188 | $2.93 \times 10^6$ | 5.69% |
| 8 | 5% Kollidon 30 | $2.76 \times 10^5$ | 0.54% |
| 9 | Poloxamer + Kollidon 30 | $7.00 \times 10^3$ | 0.01% |

Example 5

This study was performed to evaluate lyophilization parameters in the freeze-drying trays (e.g., GORE® Lyoguard® freeze-drying trays) that would be used for scaling up the lyophilization process for manufacturing. The previous studies described in Examples 1~4 were performed in 20 mL vials. An engineering batch of Strain 3 (*Ruminococcus torques*) was compared to a tray of formulation buffer in separate freeze-drying trays.

Figure 6:
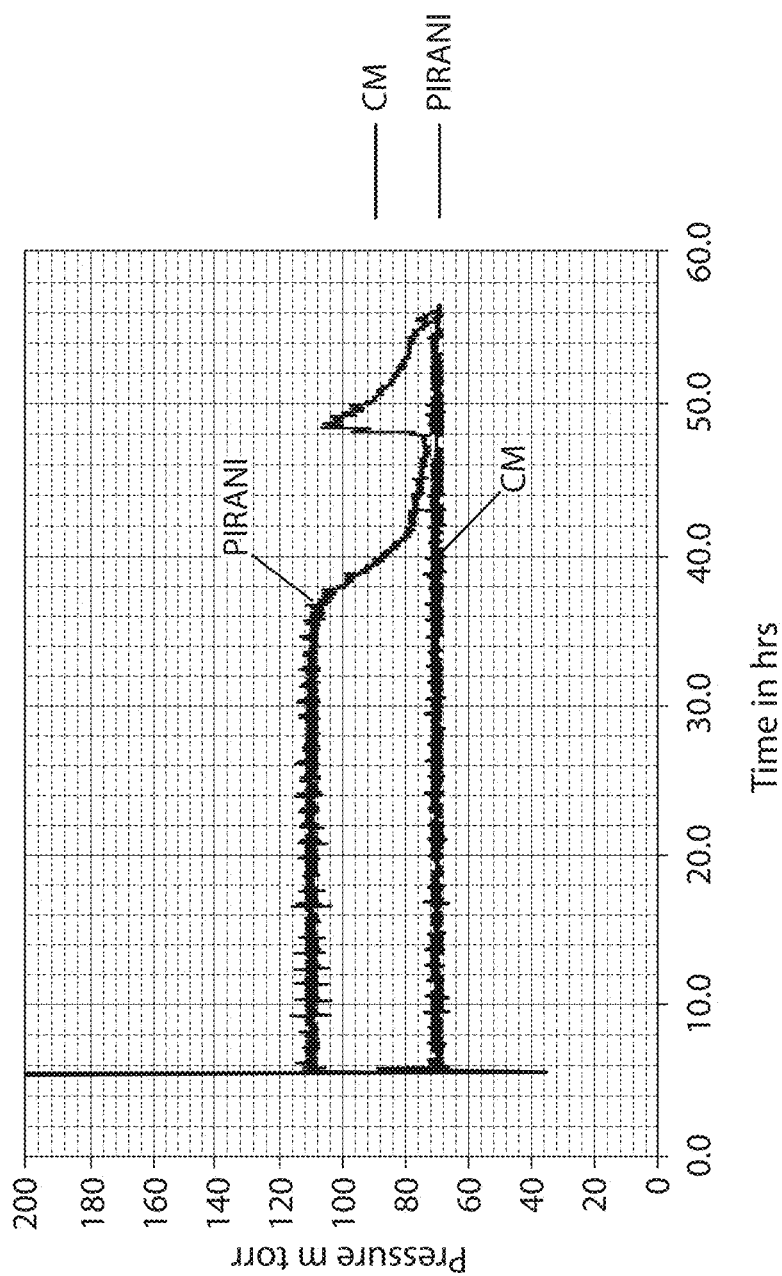
FIG. 6 shows a graph of the pressure during the lyophilization cycle described in Example 5.

The bacterial culture was grown in a 10 Liter fermenter volume which was diafiltered into the 7% Sucrose, 1% Yeast Extract, 0.05% L-Cysteine, 20 mM Histidine, pH 7.0 formulation buffer. The freeze-drying trays were filled with a volume of 750 mL. The lyophilization cycle was run with the ramp rate of 1° C. per minute. The lyophilization cycle data is shown in FIG. 6. The pressure profile shows the pirani pressure reached 70 mTorr at 48 hrs. The bound water was removed during the secondary drying and the pirani reaches 70 mTorr at 57 hours. The appearance of the freeze-drying trays after lyophilization showed lyophilization cakes that were intact and not collapsed (data not shown), demonstrating the adequacy of the cycle. The primary drying step using 70 mTorr and −10° C. along with a secondary drying step using 70 mTorr and 20° C. successfully lyophilized strain 3 in the freeze-draying trays. This scaled up process for lyophilizing bacterial compositions can be applied to the other bacterial strains.

Example 6

Additional studies were performed to evaluate bacterial recovery using 0.05% sodium metabisulfite as an excipient in the formulation and an increased temperature ramp of 2.5° C./min. A culture of bacterial strain 2 (*Anaerotruncus colihominis*) was inoculated in a 500 mL centrifuge bottle with a 1 mL cryovial. The culture was grown overnight and harvested at an OD of 0.325. This bacteria were spun down and washed with the a lyophilization formulation buffer containing 7% sucrose, 1% yeast extract, 0.05% cysteine, 0.05% sodium metabisulfite, and 20 mM histidine. The bacteria were pelleted again, the supernatant was discarded, and the pellet was resuspended in a final volume of 100 mL of the same lyophilization formulation buffer. Seven milliliters of the resuspension were aliquoted into 20 mL vials and lyophilized using a temperature ramp rate of 2.5° C./min between temperature hold points.

The viability of strain 2 before lyophilization was measured as $6.4 \times 10^8$ CFU/mL. The viability after lyophilization was $1.93 \times 10^8$ CFU/mL, resulting in a viability of 30%. This was an improved yield from previous runs, so the formulation buffer selected for strain 2 included 0.05% sodium metabisulfite as an excipient. The freezing rate of 2.5° C./min was selected for strain 2 based on this run, which was used as the rate of temperature ramp rate between all steps during lyophilization.

Formulations and lyophilization cycle conditions for each of bacterial strains 1-8 are shown in Table 13.

TABLE 13

Lyophilization formulations and conditions

| Bacterial Strain* | Formulation | Temperature Ramp Rate | Primary Drying | Secondary Drying |
|---|---|---|---|---|
| 1 | 7% Sucrose, 1% Yeast Extract, 0.05% L-Cysteine, 0.05% Sodium Metabisulfite, 20 mM Histidine, pH 7.0 | 2.5° C./min | −10° C./ 70 mTorr | 20° C./ 70 mTorr |
| 2 | 7% Sucrose, 1% Yeast Extract, 0.05% L-Cysteine, 0.05% Sodium Metabisulfite, 20 mM Histidine, pH 7.0 | 2.5° C./min | −10° C./ 70 mTorr | 20° C./ 70 mTorr |
| 3 | 7% Sucrose, 1% Yeast Extract, 0.05% L-Cysteine, 20 mM Histidine, pH 7.0 | 1° C./min | −10° C./ 70 mTorr | 20° C./ 70 mTorr |
| 4 | 7% Sucrose, 1% Yeast Extract, 0.05% L-Cysteine, 20 mM Histidine, pH 7.0 | 1° C./min | −10° C./ 70 mTorr | 20° C./ 70 mTorr |
| 5 | 7% Sucrose, 1% Yeast Extract, 0.05% L-Cysteine, 20 mM Histidine, pH 7.0 | 1° C./min | −10° C./ 70 mTorr | 20° C./ 70 mTorr |
| 6 | 7% Sucrose, 1% Yeast Extract, 0.05% L-Cysteine, 0.05% Sodium Metabisulfite, 20 mM Histidine, pH 7.0 | 2.5° C./min | −10° C./ 70 mTorr | 20° C./ 70 mTorr |
| 7 | 7% Sucrose, 1% Yeast Extract, 0.05% L-Cysteine, 20 mM Histidine, pH 7.0 | 1° C./min | −10° C./ 70 mTorr | 20° C./ 70 mTorr |
| 8 | 7% Sucrose, 1% Yeast Extract, 0.05% L-Cysteine, 20 mM Histidine, pH 7.0 | 1° C./min | −10° C./ 70 mTorr | 20° C./ 70 mTorr |

*Strain numbering corresponds to Table 7.

What is claimed is:

1. A method for preserving bacteria, the method comprising:
   (i) adding bacteria to a composition comprising a disaccharide, yeast extract, cysteine, sodium metabisulfite, and a histidine buffer; and
   (ii) subjecting the composition comprising the bacteria to a lyophilization cycle.

2. The method of claim 1, wherein the lyophilization cycle comprises one or more steps of a temperature ramp rate between 0.5° C./min to 3° C./min.

3. The method of claim 2, wherein the temperature ramp rate is 1° C./min.

4. The method of claim 2, wherein the temperature ramp rate is 2.5° C./min.

5. The method of claim 1, wherein the method further comprises measuring the number of colony forming units after subjecting the composition comprising the bacteria to the lyophilization cycle.

6. The method of claim 5, wherein the method further comprises measuring the number of colony forming units prior to subjecting the composition comprising the bacteria to the lyophilization cycle.

7. The method of claim 6, wherein the method further comprises:
   comparing the number of colony forming units prior to subjecting the composition comprising the bacteria to the lyophilization cycle and the number of colony forming units after subjecting the composition comprising the bacteria to the lyophilization cycle; and
   determining a percentage of recovered colony forming units of the bacteria after the lyophilization cycle.

8. The method of claim 1, wherein the composition maintains viability of one or more bacterial strains upon lyophilization.

9. The method of claim 1, wherein the method allows for recovery of at least 10% of colony forming units of the bacteria over a period of time.

10. The method of claim 9, wherein the period of time is at least 2 weeks.

11. The method of claim 1, wherein the method allows for recovery of at least 10% of colony forming units of the bacteria after a freeze-thaw cycle.

12. The method of claim 1, wherein the method allows for recovery of at least 10% of colony forming units of the bacteria after the lyophilization cycle.

13. The method of claim 1, wherein the bacteria comprise one or more bacterial strains belonging to the class Clostridia.

14. The method of claim 1, wherein the bacteria comprise one or more bacterial strains belonging to the family Clostridiaceae.

15. The method of claim 1, wherein the bacteria comprise one or more bacterial strains belonging to *Clostridium* clusters IV and/or XIVa.

16. The method of claim 1, wherein the bacteria comprise one or more bacterial strains belonging to species selected from the group consisting of *Clostridium bolteae, Anaerotruncus colihominis, Ruminococcus torques, Clostridium symbiosum, Blautia producta, Dorea longicatena, Erysipelotrichaceae bacterium* and *Subdolinogranulum* spp.

17. The method of claim 1, wherein the disaccharide is trehalose.

18. The method of claim 17, wherein the composition comprises about 7.5% trehalose, about 1% yeast extract, about 0.05% cysteine, about 0.05% sodium metabisulfite, and about 20 mM histidine buffer.

19. The method of claim 1, wherein the disaccharide is sucrose.

20. The method of claim 19, wherein the composition comprises 7.0% sucrose, 1% yeast extract, 0.05% cysteine, 0.05% sodium metabisulfite, and 20 mM histidine buffer.

* * * * *